US010239889B1

(12) United States Patent
Ohashi et al.

(10) Patent No.: US 10,239,889 B1
(45) Date of Patent: Mar. 26, 2019

(54) PENTACYCLIC COMPOUND

(71) Applicant: Eisai R&D Management Co., Ltd., Bunkyo-ku, Tokyo (JP)

(72) Inventors: Yoshiaki Ohashi, Tsukuba (JP); Yoshihiko Norimine, Tsukuba (JP); Tamaki Hoshikawa, Tsukuba (JP); Yu Yoshida, Tsukuba (JP); Yoshihisa Kobayashi, Tokyo (JP); Nobuhiro Sato, Tsukuba (JP); Koji Hagiwara, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 16/122,116

(22) Filed: Sep. 5, 2018

(30) Foreign Application Priority Data

Sep. 7, 2017 (JP) .................................. 2017-172169

(51) Int. Cl.
| | | |
|---|---|---|
| *A61K 31/551* | (2006.01) | |
| *A61P 25/00* | (2006.01) | |
| *C07D 495/22* | (2006.01) | |
| *A61P 25/16* | (2006.01) | |
| *A61P 25/28* | (2006.01) | |

(52) U.S. Cl.
CPC ............ *C07D 495/22* (2013.01); *A61P 25/16* (2018.01); *A61P 25/28* (2018.01)

(58) Field of Classification Search
CPC ....... A61K 31/551; A61P 25/00; C07D 495/22
USPC ........................................... 514/219; 540/492
See application file for complete search history.

(56) References Cited

U.S. PATENT DOCUMENTS

| 4,187,306 A | 2/1980 | Mayer et al. |
| 5,859,016 A | 1/1999 | Suh et al. |

FOREIGN PATENT DOCUMENTS

| JP | S54-024896 | 2/1979 |
| JP | H9-118621 | 5/1997 |

OTHER PUBLICATIONS

Allen B et al., "Abundant tau filaments and nonapoptotic neurodegeneration in transgenic mice expressing human P301S tau protein", The Journal of Neuroscience, Nov. 1, 2002 vol. 21, p. 9340-p. 9351.
Bruce AP. et al., "Choline acetyltransferase activity and cognitive domain score of Alzheimer's patients", Neurobiology of Aging, 2000 vol. 21, p. 11-p17.
Daniel Dautan D. et al., "A major external source of cholinergic innervation of the striatum and nucleus accumbens originates in the brainstem", The Journal of Neuroscience, 2014 vol. 34 No. 13, p. 4509-p. 4518.

(Continued)

*Primary Examiner* — Brenda L Coleman
(74) *Attorney, Agent, or Firm* — Fish & Richardson P.C.

(57) ABSTRACT

The present invention provides compounds represented by formulas (1) to (VI) or pharmaceutically acceptable salts thereof:

12 Claims, No Drawings

(56) References Cited

OTHER PUBLICATIONS

Everitt BJ et al., "Central cholinergic systems and cognition", Annu. Rev. Psychol., 1997 vol. 48, p. 649-p. 684.
Fischer W. et al., "Progressive decline in spatial learning and integrity of forebrain cholinergic neurons in rats during aging", Neurobiology of Aging, 1992 vol. 13, p. 9-p. 23.
Gilmor ML et al., "Coordinate expression of the vesicular acetylcholine transporter and choline acetyltransferase following septohippocampal pathway lesions", Journal of Neurochemistry, 1998 vol. 71, p. 2411-p. 2420.
Gómez-Isla T et al., "Neuronal loss correlates with but exceeds neurofibrillary tangles in Alzheimer's disease", American Neurological Association, 1997 vol. 41, p. 17-p. 24.
Gu H et al., "Recombinant human NGF-loaded microspheres promote survival of basal forebrain cholinergic neurons and improve memory impairments of spatial learning in the rat model of Alzheimer's disease with fimbria-fornix lesion", Neuroscience Letters, 2009 vol. 453, p. 204-p. 209.
Gulledge AT. et al., "Cholinergic inhibition of neocortical pyramidal neurons", J. Neurosci., 2005 vol. 25, p. 10308-p. 10320.
Hoffmann NA et al., "Impaired plasticity of cortical dendritic spines in P301S tau transgenic mice", Acta Neuropathol Communications, Jan. 2013 (82).
Lapchak PA et al., "Effect of recombinant human nerve growth factor on presynaptic cholinergic function in rat hippocampal slices following partial septohippocampal lesions: measures of [3H]acetylcholine synthesis, [$^3$H]acetylcholine release and choline acetyltransferase activity", Neuroscience, 1991 vol. 42, p. 639-p. 649.
Leanza G. et al., "Selective immunolesioning of the basal forebrain cholinergic system disrupts short-term memory in rats", European Journal of Neuroscience, 1996 vol. 8, p. 1535-p. 1544.
Leanza G. et al., "Selective lesioning of the basal forebrain cholinergic system by intraventricular 192IgG-saporin: behavioural, biochemical and stereological studies in the rat", European Journal of Neurosceience, 1995 vol. 7, p. 329-p. 343.
Lee VM et al., "Neurodegenerative tauopathies", Annu. Rev. Neurosci, 2001 vol. 24, p. 1121-p. 1159.
Lowe S et al., "Effects of a novel mGlu2/3 receptor agonist prodrug, LY2140023 monohydrate, on central monoamine turnover as determined in human and rat cerebrospinal fluid", Psychopharmacology, 2012 vol. 219, p. 959-p. 970.
M Steriade M. et al., "Neuronal Activities in Brain-Stem Cholinergic Nuclei Related to Tonic Activation Processes in Thalamocortical Systems", The Journal Neuroscience, Aug. 1990 vol. 10 No. 8, p. 2541-p. 2559.
Mori E. et al., "Donepezil for dementia with Lewy bodies: a randomized, placebo-controlled trial", American Neurological Association, 2012 vol. 72 , p. 41-p. 52.
Mufson EJ. et al., "Cholinergic system during the progression of Alzheimer's disease : therapeutic implication", Expert Rev Neurother, 2008 vol. 8, p. 1703-p. 1718.
Mufson EJ. et al., "Human cholinergic basal forebrain : chemoanatomy and neurologic dysfunction", Journal of Chemical Neuroanatomy, 2003 vol. 26, p. 233-p. 242.
Ogura H. et al., "Donepezil, a centrally acting acetylcholinesterase inhibitor, alleviates learning deficits in hypocholinergic models in rats", Methods Find Exp Clin Pharmacol, 2000 vol. 22 No. 2, p. 89-p. 95.
Onishi T et al., "Early-onset cognitive deficits and axonal transport dysfunction in P301S mutant tau transgenic mice", Neuroscience Research, 2014 vol. 80, p. 76-p. 85.
Perry, E. K. et. al., "Neocortical cholinergic activities differentiate Lewy body dementia from classical Alzheimer's disease", Clinical Neuroscience and Neuropathology, 1994 vol. 5, p. 747-p. 749.
Rogers SL. et al., "The efficacy and safety of donepezil in patients with Alzheimer's disease: results of a US Multicentre, Randomized, Double-Blind, Placebo-Controlled Trial", Dementia, 1996 vol. 7, p. 293-p. 303.
Salehi A et al., "Increased App Expression in a Mouse Model of Down's Syndrome Disrupts NGF Transport and Causes Cholinergic Neuron Degeneration", Neuron, Jul. 6, 2006 vol. 51, p. 29-p. 42.
Schliebs R. et al., "The significance of the cholinergic system in the brain during aging and in Alzheimer's disease", J. Neural. Transm , 2006 vol. 113, p. 1625-p. 1644.
Shimada, H. et al., "Mapping of brain acetylcholinesterase alterations in Lewy body disease by PET", Neurology, 2009 vol. 73, p. 273-p. 278.
Spowart-Manning L. et al., "Spatial discrimination deficits by excitotoxic lesions in the Morris waterescape task", Behavioural Brain Research, 2005 vol. 156, p. 269-p. 276.
Tiraboschi, P. et al., "Cholinergic dysfunction in diseases with Lewy bodies", Neurology, 2000 vol. 54, p. 407-p. 411.
Vana L et al., "Progression of tau pathology in cholinergic Basal forebrain neurons in mild cognitive impairment and Alzheimer's disease", The American Journal of Pathology, Nov. 2011 vol. 179 No. 5, p. 2533-p. 2550.
Xu H et al., "Memory deficits correlate with tau and spine pathology in P301S MAPT transgenic mice", Neuropathology and Applied Neurobiology, 2014 vol. 40, p833-p843.
Xu W et al., "Amyloid precursor protein-mediated endocytic pathway disruption induces axonal dysfunction and neurodegeneration", The Journal of Clinical Investigation, 2016 vol. 126, p. 1815-p. 1833.
Yoshiyama Y et al., "Synapse loss and microglial activation precede tangles in a P301S tauopathy model", Neuron, Feb. 1, 2007 vol. 53, p. 337-p. 351.
Decker, "Novel inhibitors of acetyl-and butyrylcholinesterase derived from the alkaloids dehydroevodiamine and rutaecarpine," European Journal of Medicinal Chemistry, vol. 40, No. 3, ISSN 0223-5234, 2005, p. 305-p. 313.
Huang et al., "A simple heterocyclic fusion reaction and its application for expeditious syntheses of rutaecarpine and its analogs," Tetrahedron Letters, vol. 55, No. 26, 2014, p. 3607-p. 3609.
International Search Report in International Application No. PCT/JP2018/032797, dated Dec. 4, 2018, 12 pages (with English Translation).
Ustalar et al., "Microwave assisted synthesis of 2,3-dihydro-4H-benzo[4,5]thiazolo[3,2-a]furo[2,3-d]pyrimidin-4-ones and 6,7-dihydro-5H-furo[2,3-d]thiazolo[3,2-a]pyrimidin-5-ones using Mn(OAc)$_3$ ," Tetrahedron Letters, vol. 58, No. 6, ISSN 0040-4039, Dec. 24, 2016, p. 516-p. 519.

PENTACYCLIC COMPOUND

CROSS-REFERENCE TO RELATED APPLICATION

This application claims the benefit of Japanese patent application No. 2017-172169 filed on Sep. 7, 2017, the disclosure of which is herein incorporated by reference in its entirety.

TECHNICAL FIELD

The present invention relates to a pentacyclic compound or a pharmaceutically acceptable salt thereof having cholinergic neuron activation and/or neuroprotective effect, and pharmaceutical use thereof. The present invention also relates to pharmaceutical compositions comprising the above compound as an active ingredient.

BACKGROUND

Cholinergic neurons which release acetylcholine as a transmitter are widely projected in the forebrain from the nucleus basalis of Meynert and the septal nucleus of the basal forebrain to the hippocampus, amygdala, and cerebral cortex, and are involved in the modulation of memory, learning, cognition, and attention (Non-Patent Literature 1). Moreover, cholinergic neurons in the pedunculopontine tegmental nucleus and laterodorsal tegmental nucleus of the brain stem are projected in the striatum, accumbens nucleus, substantia nigra, and thalamus, and are considered to be involved in the control of motivation and vigilance (Non-Patent Literatures 2 to 4).

In particular, the role of cholinergic neurons in the basal forebrain has been more clarified by analysis using many animal models such as lesion model. Especially, the correlation between functional disorder of cholinergic neurons and decreased memory and learning has been shown in the animal models (Non-Patent Literatures 5 to 7), and it has been shown that cognitive performance is improved by increasing the amount of acetylcholine using a cholinesterase inhibitor, and enhancing the function of cholinergic neurons (Non-Patent Literatures 8 to 12).

It has been reported that Nerve Growth Factor (NGF) shows the neuroprotective effect on cholinergic neurons in the animal model indicating loss of cholinergic neurons. (Non-Patent Literature 13 to 15).

Particularly for Alzheimer's disease (AD), loss of cholinergic neurons is found from early stage of AD and is one of the pathological features of AD. Accumulation of senile plaques by deposits of amyloid beta and neurofibrillary tangles by tau protein aggregation are also pathological features of AD, and particularly neurofibrillary tangles are known to increase with the progress of the disease status and bring neuronal death. Neurofibrillary tangles are found in nucleus basalis of Meynert and entorhinal cortex from the early stage of AD. Among them, it is reported that loss of cholinergic neurons in nucleus basalis of Meynert by tau protein aggregation is found at earlier stage and that there is a correlation between the loss and a decrease in cognitive function score (Non-Patent Literatures 16 and 17). Similarly to AD, hyperphosphorylation and abnormal accumulation of tau protein is found in genetically modified mice having a P301S mutation which has been found in familial frontotemporal dementia (human tau P301S transgenic mice). Consequently, neurofibrillary tangles, a pathological feature of AD, are formed (Non-Patent Literature 18) and bring cognitive dysfunction by synaptic impairment, neurodegeneration and loss of neurons. Based on these findings, human tau P301S transgenic mice are widely used as AD-like animal models (Non-Patent Literatures 19-22), and improvement of cognitive decline and suppression of disease status progress in Alzheimer's disease can be expected by suppressing AD-like pathological changes in human tau P301S transgenic mice.

Furthermore, multiple analyses using genetically modified mice and animal models of disorders suggest that axonal transport deficit is one of the causes of loss of cholinergic neurons (Non-Patent Literatures 23-25). Among them, the axon of cholinergic neurons which projects from septal area to hippocampus is impaired in a fimbria-fornix lesioned model and impairment of retrograde transport of molecules involved with survival and function brings loss of neurons (Non-Patent Literatures 26-28). The impairment of retrograde transport is found also in genetically modified mice (Non-Patent Literatures 23 and 24) and loss of cholinergic neurons by fimbria-fomrnix lesion reflects one aspect of the disease status. Accordingly, improvement of cognitive decline and suppression of disease status progress in Alzheimer's disease can be expected by suppression or improvement of loss of cholinergic neurons in this model of the disorder.

Dementia with Lewy bodies (DLB) and Parkinson disease (PD) are progressive neurodegenerative disorders in which abnormal inclusion bodies (Lewy bodies) mainly composed of alpha synuclein appear in neurons and bring degeneration and loss of neurons. Cognitive dysfunction develops if Lewy bodies are mainly distributed in cerebral cortex and Parkinsonism develops if Lewy bodies are mainly distributed in brain stem. In addition to that, psychiatric symptoms such as visual hallucination, hallucination and delusion, sleep disorder and autonomic symptoms also develop. The diagnosis is dementia with Lewy bodies if dementia appears before or within one year from the onset of Parkinsonism and the diagnosis is Parkinson disease with dementia (PDD) if Parkinsonism has appeared before one year or more from the onset of dementia. Dementia with Lewy bodies, Parkinson disease with dementia and Parkinson disease are pathologically same diseases and comprehensively referred to as Lewy body disease (LBD) though these are different in cognitive dysfunction and appearance order and degree of Parkinsonism. In dementia with Lewy bodies and Parkinson disease with dementia, similarly to Alzheimer's disease, neurons of nucleus basalis of Meynert, a nuclei of origin of cholinergic nerve, are degenerated and lost and it is reported that severe cholinergic neuron disorder appears in hippocampus and cortex (Non-Patent Literatures 29-31). Furthermore, there is a correlation between progress of cholinergic neuron disorder and cognitive dysfunction (Non-Patent Literature 29), and cholinesterase inhibitors have been demonstrated to improve cognitive function. Based on these findings, cognitive function improves by the improvement of function of cholinergic neurons, and similarly to Alzheimer's disease, improvement of cognitive decline and suppression of disease status progress in dementia with Lewy bodies and Parkinson disease with dementia can be expected by suppression or improvement of loss of cholinergic neurons in several models of the disorder.

Therefore, based on these findings, an improvement in reduced cognitive performance caused by the dysfunction of cholinergic neurons can be expected by achieving functional activation and/or neuroprotective effect on cholinergic neurons in clinical practice.

In addition to the above diseases, examples of diseases for which association between decrease in cognitive function and the dysfunction of cholinergic neurons has been reported include Huntington's chorea, Down's syndrome, amyotrophic lateral sclerosis (ALS), major depression, schizophrenia, and the like.

CITATION LIST

Non-Patent Literature

[Non-Patent Literature 1] Everitt B J et al. "Central cholinergic systems and cognition." Annu. Rev. Psychol. 48 (1997) 649-684.
[Non-Patent Literature 2] Gulledge A T. et al. "Cholinergic inhibition of neocortical pyramidal neurons." J. Neurosci. 25 (2005) 10308-20.
[Non-Patent Literature 3] Daniel Dautan D. et al. "A major external source of cholinergic innervation of the striatum and nucleus accumbens originates in the brainstem." J. Neurosci. 34 (2014) 4509-18.
[Non-Patent Literature 4] M Steriade M. et al. "Neuronal activities in brain-stem cholinergic nuclei related to tonic activation processes in thalamocortical systems." J. Neurosci. 10 (1990) 2541-59.
[Non-Patent Literature 5] Fischer W. et al. "Progressive decline in spatial learning and integrity of forebrain cholinergic neurons in rats during aging." Neurobiol. Aging 13 (1992) 9-23.
[Non-Patent Literature 6] Leanza G. et al. "Selective lesioning of the basal forebrain cholinergic system by intraventricular 192 IgG-saporin: behavioural, biochemical and stereological studies in the rat." Eur. J. Neurosci. 7 (1995) 329-43.
[Non-Patent Literature 7] Leanza G. et al. "Selective immunolesioning of the basal forebrain cholinergic system disrupts short-term memory in rats." Eur. J. Neurosci. 8 (1996) 1535-44.
[Non-Patent Literature 8] Ogura H. et al. "Donepezil, a centrally acting acetylcholinesterase inhibitor, alleviates learning deficits in hypocholinergic models in rats." Methods Find Exp Clin Pharmacol. 22 (2000) 89-95.
[Non-Patent Literature 9] Spowart-Manning L. et al. "Spatial discrimination deficits by excitotoxic lesions in the Morris water escape task." Behav Brain Res. 156 (2005) 269-76.
[Non-Patent Literature 10] Bruce A P. et al. "Choline acetyltransferase activity and cognitive domain score of Alzheimer's patients." Neurobiol. Aging. 21(2000) 11-17
[Non-Patent Literature 11] Rogers S L. et al. "The efficacy and safety of donepezil in patients with Alzheimer's disease: results of a US Multicentre, Randomized, Double-Blind, Placebo-Controlled Trial. The Donepezil Study Group." Dementia. 7 (1996) 293-303
[Non-Patent Literature 12] Mori E. et al. "Donepezil for dementia with Lewy bodies: a randomized, placebo-controlled trial." Ann Neurol. 72 (2012) 41-52
[Non-Patent Literature 13] Mufson E J. et al. "Human cholinergic basal forebrain: chemoanatomy and neurologic dysfunction." J. Chem. Neuroanat. 26 (2003) 233-242
[Non-Patent Literature 14] Mufson E J. et al. "Cholinergic system during the progression of Alzheimer's disease: therapeutic implication." Expert. Rev. Neurother. 8 (2008) 1703-1718
[Non-Patent Literature 15] Schliebs R. et al. "The significance of the cholinergic system in the brain during aging and in Alzheimer's disease." J. Neural. Transm 113 (2006) 1625-1644
[Non-Patent Literature 16] Vana L et al. "Progression of tau pathology in cholinergic Basal forebrain neurons in mild cognitive impairment and Alzheimer's disease." Am J Pathol. 179 (2011) 2533-2550.
[Non-Patent Literature 17] Gómez-Isla T et al. "Neuronal loss correlates with but exceeds neurofibrillary tangles in Alzheimer's disease." Ann Neurol. 41 (1997) 17-24.
[Non-Patent Literature 18] Lee V M et al. "Neurodegenerative tauopathies." Annu. Rev. Neurosci. 24 (2001) 1121-1159.
[Non-Patent Literature 19] Allen B et al. "Abundant tau filaments and nonapoptotic neurodegeneration in transgenic mice expressing human P301S tau protein." J. Neurosci. 22 (2002) 9340-9351.
[Non-Patent Literature 20] Xu H et al. "Memory deficits correlate with tau and spine pathology in P301S MAPT transgenic mice." Neuropathol. Appl. Neurobiol. 40 (2014) 833-43.
[Non-Patent Literature 21] Yoshiyama Y et al. "Synapse loss and microglial activation precede tangles in a P301S tauopathy mouse model." Neuron. 53 (2007) 337-351.
[Non-Patent Literature 22] Hoffmann N A et al. "Impaired plasticity of cortical dendritic spines in P301S tau transgenic mice." Acta Neuropathol Commun. 1 (2013) 82.
[Non-Patent Literature 23] Salehi A et al. "Increased App Expression in a Mouse Model of Down's Syndrome Disrupts NGF Transport and Causes Cholinergic Neuron Degeneration" Neuron 51 (2006) 29-42.
[Non-Patent Literature 24] Onishi T et al. "Early-onset cognitive deficits and axonal transport dysfunction inP301S mutant tau transgenic mice" Neuroscience Research 80 (2014) 76-85.
[Non-Patent Literature 25] Xu W et al. "Amyloid precursor protein-mediated endocytic pathway disruption induces axonal dysfunction and neurodegeneration" J. Clin. Invest. 126 (2016) 1815-33.
[Non-Patent Literature 26] Lapchak P A et al. "Effect of recombinant human nerve growth factor on presynaptic cholinergic function in rat hippocampal slices following partial septohippocampal lesions: measures of [$^3$H]acetylcholine synthesis, [$^3$H]acetylcholine release and choline acetyltransferase activity" Neuroscience 42 (1991) 639-49.
[Non-Patent Literature 27] Gilmor M L et al. "Coordinate expression of the vesicular acetylcholine transporter and choline acetyltransferase following septohippocampal pathway lesions" J. Neurochem. 71 (1998) 2411-20.
[Non-Patent Literature 28] Gu H et al. "Recombinant human NGF-loaded microspheres promote survival of basal forebrain cholinergic neurons and improve memory impairments of spatial learning in the rat model of Alzheimer's disease with fimbria-fornix lesion" Neurosci. Lett. 453 (2009) 204-9.
[Non-Patent Literature 29] Shimada, H. et al., "Mapping of brain acetylcholinesterase alterations in Lewy body disease by PET" Neurology, vol. 73, pp. 273-278, 2009.
[Non-Patent Literature 30] Tiraboschi, P. et al., "Cholinergic dysfunction in diseases with Lewy bodies" Neurology 54 (2000) 407-411.
[Non-Patent Literature 31] Perry, E. K. et. al., "Neocortical cholinergic activities differentiate Lewy body dementia from classical Alzheimer's disease", NeuroReport, vol. 5, pp. 747-749 (1994).

SUMMARY

An object of the present invention is to provide a compound or a pharmaceutically acceptable salt thereof having cholinergic neuron activation and/or neuroprotective effect and having a potential use of a therapeutic agent for Alzheimer's disease, dementia with Lewy bodies and Parkinson disease with dementia.

As a result of extensive studies to solve the above problems, the present inventors found a pentacyclic compound or pharmaceutically acceptable salts thereof having cholinergic neuron activation and or neuroprotective effect.

That is, the present invention relates to the following <1> to <30>.

<1> A compound selected from the group consisting of:

3-fluoro-6,11-dimethyl-6,7,10,11,12,13-hexahydrobenzo[f]pyrido[4'',3'':4',5']thieno[2',3':4,5]pyrimido[1,2-a][1,4]diazepine-5,14-dione:

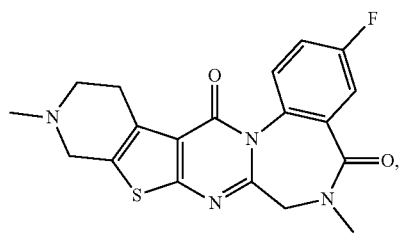

(I)

5,10-dimethyl-5,6,9,10,11,12-hexahydropyrido[4'',3'':4',5']thieno[2',3':4,5]pyrimido[1,2-a]thieno[2,3-f][1,4]diazepine-4,13-dione:

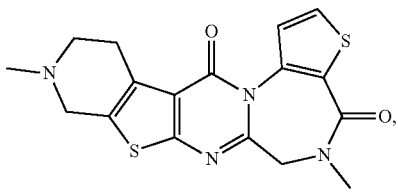

(II)

5,10-dimethyl-5,6,9,10,11,12-hexahydropyrido[4'',3'':4',5']thieno[2',3':4,5]pyrimido[1,2-a]thieno[3,2-f][1,4]diazepine-4,13-dione:

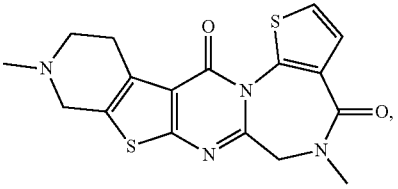

(III)

(3aS,14aR)-5,10-dimethyl-3,3a,5,6,9,10,11,12-octahydro-1H-cyclopenta[f]pyrido[4'',3'':4',5']thieno[2',3':4,5]pyrimido[1,2-a][1,4]diazepine-4,13(2H,14aH)-dione:

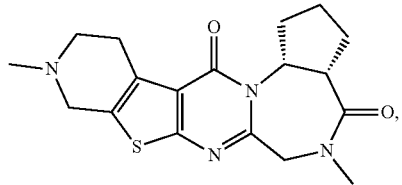

(IV)

(3aR,14aR)-5,10-dimethyl-3,3a,5,6,9,10,11,12-octahydro-1H-cyclopenta[f]pyrido[4'',3'':4',5']thieno[2',3':4,5]pyrimido[1,2-a][1,4]diazepine-4,13(2H, 14aH)-dione:

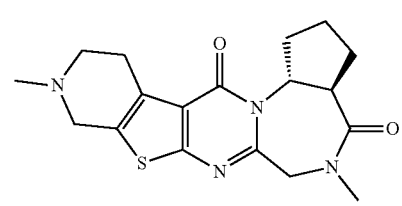

(V)

and (3aS,14aS)-5,10-dimethyl-3,3a,5,6,9,10,11,12-octahydro-1H-cyclopenta[f]pyrido[4'',3'':4',5']thieno[2',3':4,5]pyrimido[1,2-a][1,4]diazepine-4,13(2H,14aH)-dione:

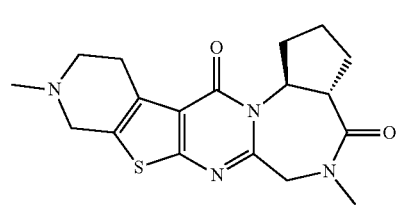

(VI)

or a pharmaceutically acceptable salt thereof.

<2> 3-Fluoro-6,11-dimethyl-6,7,10,11,12,13-hexahydrobenzo[f]pyrido[4'',3'':4',5']thieno[2',3':4,5]pyrimido[1,2-a][1,4]diazepine-5,14-dione or a pharmaceutically acceptable salt thereof:

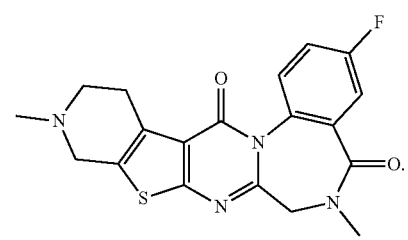

(I)

<3> 5,10-Dimethyl-5,6,9,10,11,12-hexahydropyrido[4'',3'':4',5']thieno[2',3':4,5]pyrimido[1,2-a]thieno[2,3-f][1,4]diazepine-4,13-dione or a pharmaceutically acceptable salt thereof:

<4> 5,10-Dimethyl-5,6,9,10,11,12-hexahydropyrido[4",3": 4',5']thieno[2',3':4,5]pyrimido[1,2-a]thieno[3,2-f][1,4]diazepine-4,13-dione or a pharmaceutically acceptable salt thereof:

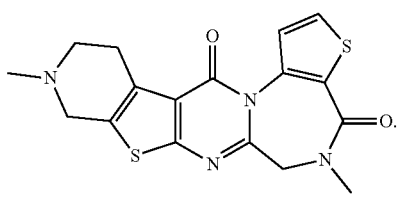

(II)

<5> (3aS,14aR)-5,10-Dimethyl-3,3a,5,6,9,10,11,12-octahydro-1H-cyclopenta[f]pyrido[4",3":4',5']thieno[2',3':4,5]pyrimido[1,2-a][1,4]diazepine-4,13(2H,14aH)-dione or a pharmaceutically acceptable salt thereof:

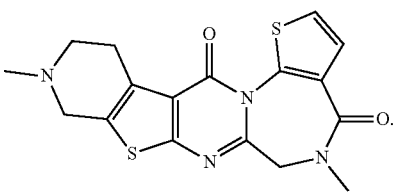

(III)

<6> (3aR,14aR)-5,10-Dimethyl-3,3a,5,6,9,10,11,12-octahydro-1H-cyclopenta[f]pyrido[4",3":4',5']thieno[2',3':4,5]pyrimido[1,2-a][1,4]diazepine-4,13(2H,14aH)-dione or a pharmaceutically acceptable salt thereof:

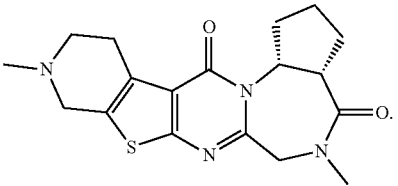

(IV)

<7> (3aS,14aS)-5,10-Dimethyl-3,3a,5,6,9,10,11,12-octahydro-1H-cyclopenta[f]pyrido[4",3":4',5']thieno[2',3':4,5]pyrimido[1,2-a][1,4]diazepine-4,13(2H,14aH)-dione or a pharmaceutically acceptable salt thereof:

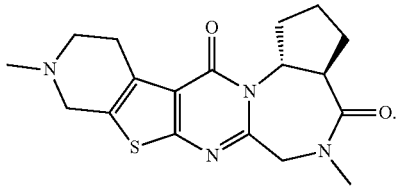

(V)

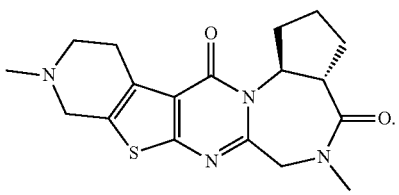

(VI)

<8> A pharmaceutical composition comprising the compound or pharmaceutically acceptable salt thereof according to any one of <1> to <7> and one or more pharmaceutically acceptable additives.

<9-1> The pharmaceutical composition according to <8>, which is a neuron activating agent.

<9-2> The pharmaceutical composition according to <8>, which is a neuron protecting agent.

<10> The pharmaceutical composition according to <8> for the treatment of cognitive dysfunction.

<11> A therapeutic agent for cognitive dysfunction comprising the compound or pharmaceutically acceptable salt thereof according to any one of <1> to <7>.

<12> A method of treating cognitive dysfunction, comprising administering the compound or pharmaceutically acceptable salt thereof according to any one of <1> to <7> to a patient in need thereof.

<13> The compound or pharmaceutically acceptable salt thereof according to any one of <1> to <7> for use in the treatment of cognitive dysfunction.

<14> Use of the compound or pharmaceutically acceptable salt thereof according to any one of <1> to <7> for the manufacture of a therapeutic agent for cognitive dysfunction.

<15> A therapeutic agent for Alzheimer's disease comprising the compound or pharmaceutically acceptable salt thereof according to any one of <1> to <7>.

<16> A method of treating Alzheimer's disease, comprising administering the compound or pharmaceutically acceptable salt thereof according to any one of <1> to <7> to a patient in need thereof.

<17> The compound or pharmaceutically acceptable salt thereof according to any one of <1> to <7> for use in the treatment of Alzheimer's disease.

<18> Use of the compound or pharmaceutically acceptable salt thereof according to any one of <1> to <7> for the manufacture of a therapeutic agent for Alzheimer's disease.

<19> A therapeutic agent for Dementia with Lewy bodies comprising the compound or pharmaceutically acceptable salt thereof according to any one of <1> to <7>.

<20> A method of treating Dementia with Lewy bodies, comprising administering the compound or pharmaceutically acceptable salt thereof according to any one of <1> to <7> to a patient in need thereof.

<21> The compound or pharmaceutically acceptable salt thereof according to any one of <1> to <7> for use in the treatment of Dementia with Lewy bodies.

<22> Use of the compound or pharmaceutically acceptable salt thereof according to any one of <1> to <7> for the manufacture of a therapeutic agent for Dementia with Lewy bodies.

<23> A therapeutic agent for Parkinson disease with dementia comprising the compound or pharmaceutically acceptable salt thereof according to any one of <1> to <7>.

<24> A method of treating Parkinson disease with dementia, comprising administering the compound or pharmaceutically acceptable salt thereof according to any one of <1> to <7> to a patient in need thereof.

<25> The compound or pharmaceutically acceptable salt thereof according to any one of <1> to <7> for use in the treatment of Parkinson disease with dementia.

<26> Use of the compound or pharmaceutically acceptable salt thereof according to any one of <1> to <7> for the manufacture of a therapeutic agent for Parkinson disease with dementia.

<27> A method of treating a disease selected from a group consisting of Alzheimer's disease, Dementia with Lewy bodies and Parkinson disease with dementia comprising administering the compound or pharmaceutically acceptable salt thereof according to any one of <1> to <7> to a patient in need thereof.

<28> The method according to <27> wherein the disease is Alzheimer's disease.

<29> The method according to <27> wherein the disease is Dementia with Lewy bodies.

<30> The method according to <27> wherein the disease is Parkinson disease with dementia.

The pentacyclic compounds represented by formulas (I) to (VI) (hereinafter referred to as "the compounds (I) to (VI)") or pharmaceutically acceptable salts thereof according to the present invention have neuron activation and/or neuroprotective effect, as shown in activity data in pharmacological test examples provided later. The compounds (I) to (VI) of the present invention lead to an improvement of cognitive performance due to their neuron activation and/or neuroprotective effect, and thus have a potential use as therapeutic agents for Alzheimer's disease, Dementia with Lewy bodies and Parkinson disease with dementia.

DETAILED DESCRIPTION

Hereinafter, the contents of the present invention will be described in detail.

In the present specification, the structural formulas of the compounds may represent specific isomers for convenience; however, the present invention may include rotational isomers and tautomers, as well as isomeric mixtures, is not limited to the formulas described for convenience, and may be any of the isomers or a mixture containing the isomers in any proportion.

Further, polymorphic crystals may also exist; however, the present invention is also not limited to any of them and may be a singly crystal form or a mixture thereof. Moreover, the present invention also includes amorphous forms, and the compounds according to the present invention include anhydrates and solvates (particularly hydrates).

The present invention also includes isotope-labeled compounds of the compounds (I) to (VI). The isotope-labeled compounds are the same as the compounds (I) to (VI), except that one or more atoms are replaced by one or more atoms having an atomic mass or mass number different from those generally found in nature. Examples of isotopes that can be incorporated into the compounds of the present invention include isotopes of hydrogen, carbon, nitrogen, oxygen, fluorine, phosphorus, sulfur, iodine, and chlorine, and specifically include $^2H$, $^3H$, $^{11}C$, $^{14}C$, $^{15}N$, $^{18}O$, $^{18}F$, $^{32}P$, $^{35}S$, $^{123}I$, $^{125}I$, and the like.

The above isotope-labeled compounds, for example, compounds into which radioactive isotopes, such as $^3H$ and/or $^{14}C$, are incorporated, are useful for the tissue distribution assay of medicines and/or substrates. $^3H$ and $^{14}C$ are considered to be useful because of the ease of the preparation and detection thereof. Isotopes $^{11}C$ and $^{18}F$ are considered to be useful for PET (positron emission tomography), isotope $^{125}I$ is considered to be useful for SPECT (single-photon emission computed tomography), and all of them are useful for brain imaging. Replacement by heavier isotopes, such as $^2H$, results in some types of therapeutic advantages, including an increase in the in vivo half-life period or a decrease in the required dose due to higher metabolic stability, and is therefore considered to be useful under certain situations. The above isotope-labeled compounds can be similarly prepared by carrying out the procedures disclosed in the following Examples using easily usable reagents labeled with isotopes in place of reagents not labeled with isotopes.

The "pharmaceutically acceptable salts" in the present specification are not particularly limited as long as they are salts formed with the compounds according to the present invention, and specific examples include acid addition salts, such as inorganic acid salts, organic acid salts, and acidic amino acid salts.

The "pharmaceutically acceptable salt" in the present specification is any salt formed in a suitable ratio unless there is any especially limiting description, and the number of acid molecules per molecule of the compound in the formed salt is not particularly limited; however, it is preferable that the number of acid molecules per molecule of the compound be about 0.5 to about 2, and it is more preferable that the number of acid molecules per molecule of the compound be about 0.5, about 1, or about 2.

Preferable examples of the inorganic acid salts include hydrochloride, hydrobromide, sulfate, nitrate, and phosphate; and preferable examples of organic acid salts include acetate, succinate, fumarate, maleate, tartrate, citrate, lactate, stearate, benzoate, methanesulfonate, p-toluenesulfonate, and benzenesulfonate.

Preferable examples of the acidic amino acid salts include aspartate and glutamate.

When the compounds (I) to (VI) according to the present invention are obtained in a free form, they can be converted into salts that may be formed by the compounds (I) to (VI) or hydrates thereof in accordance with a conventional method.

When the compounds (I) to (VI) according to the present invention are obtained as salts of the compounds (I) to (VI) or hydrates of the compounds (I) to (VI), they can be converted into free forms of the compounds (I) to (VI) in accordance with a conventional method.

Moreover, various isomers (e.g., optical isomers, rotational isomers, stereoisomers, etc.) obtained from the compounds (I) to (VI) according to the present invention can be purified and isolated by general separation means, such as recrystallization, diastereomeric salt method, enzymatic resolution method, and various chromatographic techniques (e.g., thin-layer chromatography, column chromatography, gas chromatography, etc.).

[Pharmaceutical Preparation]

The pharmaceutical composition according to the present invention can be produced by mixing pharmaceutically acceptable additives with a compound selected from the group of compounds (I) to (VI) or pharmaceutically acceptable salts thereof. The pharmaceutical composition according to the present invention can be produced by a known method, for example, the method described in the General Rules for Preparations of The Japanese Pharmacopoeia Seventeenth Edition.

The pharmaceutical composition according to the present invention can be appropriately administered to a patient depending on the dosage form thereof.

The dose of the compounds (1) to (VI) according to the present invention or pharmaceutically acceptable salts thereof varies depending on the severity of symptoms, age, sex, body weight, dosage form, type of salt, specific type of disease, and other conditions; however, in general, the dose for an adult per day by oral administration is about 30 kg to 10 g, preferably 100 µg to 5 g, and more preferably 100 µg to 1 g; the dose for an adult per day by injection administration is about 30 µg to 1 g, preferably 100 µg to 500 mg, and more preferably 100 µg to 300 mg; and the above dose is administered once or several times.

The compounds of the present invention can be used as chemical probes for capturing the target proteins of bioactive low-molecular-weight compounds. That is, the compounds of the present invention can be converted into affinity chromatography probes, photoaffinity probes, etc., by introducing labeling groups, linkers, or the like into a moiety different from a structural moiety essential for the development of the activity of the compounds using a method described, for example, in J. Mass Spectrum. Soc. Jpn. Vol. 51, No. 5, 2003, pp. 492-498, WO2007/139149, or the like.

Examples of labeling groups, linkers, etc., used in chemical probes include groups shown in the group consisting of the following (1) to (5):
(1) protein-labeling groups, such as photoaffinity-labeling groups (e.g., a benzoyl group, a benzophenone group, an azide group, a carbonylazide group, a diaziridine group, an enone group, a diazo group, a nitro group, etc.) and chemical affinity groups (e.g., a ketone group in which the alpha carbon atom is replaced by a halogen atom, a carbamoyl group, an ester group, an alkylthio group, a Michael acceptor such as α,β-unsaturated ketone or ester, and an oxirane group);
(2) cleavable linkers, such as —S—S—, —O—Si—O—, monosaccharides (a glucose group, a galactose group, etc.), or disaccharides (lactose, etc.); and oligopeptide linkers cleavable by enzyme reaction;
(3) fishing tag groups, such as biotin and a 3-(4,4-difluoro-5,7-dimethyl-4H-3a,4a-diaza-4-bora-s-indacen-3-yl)propionyl group;
(4) radioactive labeling groups, such as $^{125}$I, $^{32}$P, $^{3}$H, and $^{14}$C; fluorescent labeling groups, such as fluorescein, rhodamine, dansyl, umbelliferone, 7-nitrofurazanyl, and a 3-(4,4-difluoro-5,7-dimethyl-4H-3a,4a-diaza-4-bora-s-indacen-3-yl)propionyl group; chemiluminescent groups, such as luciferin and luminol; and markers capable of detecting heavy metal ions, such as lanthanoid metal ions and radium ions; or
(5) groups to be attached to solid carriers, such as glass beads, glass beds, microtiter plates, agarose beads, agarose beds, polystyrene beads, polystyrene beds, nylon beads, and nylon beds.

Probes prepared by introducing labeling groups, etc., selected from the group consisting of the above (1) to (5) into the compounds of the present invention by the methods described in the above documents or the like can be used as chemical probes for identifying labeled proteins useful to search novel drug design targets, etc.

EXAMPLES

The compounds (I) to (VI) of the present invention can be produced by, for example, the methods described in the following Examples, and the effects of the compounds can be confirmed by the methods described in the following Test Examples. However, these are just examples, and the present invention is not limited to the following specific examples in any case and may be modified within a range that does not depart from the scope of the present invention.

Compounds described with document names, etc., indicate that the compounds were produced according to the documents, etc.

Moreover, the abbreviations used in the present specification are well-known and common to a person skilled in the art. In the present specification, the following abbreviations are used.
DCE: 1,2-dichloroethane
DCM: dichloromethane
DIPEA: N,N-diisopropylethylamine
DMT-MM: 4-(4,6-dimethoxy-1,3,5-triazin-2-yl)-4-methylmorpholinium chloride
DMSO: dimethylsulfoxide
EDC: 1-ethyl-3-(3-dimethylaminopropyl)carbodiimide hydrochloride
HATU: O-(7-azabenzotriazol-1-yl)-N,N,N',N'-tetramethyluronium hexafluorophosphate
HOBT: 1-hydroxybenzotriazole
n-: normal
NMM: N-methylmorpholine
t-: tertiary
TBD: 1,3,4,6,7,8-hexahydro-2H-pyrimido[1,2-a]pyrimidine
TBME: tertiary butyl methyl ether
TEA: triethylamine
THF: tetrahydrofuran
$^{1}$H-NMR: proton nuclear magnetic resonance spectrometry
MS: mass spectrometry
HPLC: high-performance liquid chromatography The term "room temperature" in the following Examples and Production Examples generally refers to about 10° C. to about 35° C. % refers to weight percent unless otherwise specified.

Chemical shifts of proton nuclear magnetic resonance spectra are denoted in δ-unit (ppm) relative to tetramethylsilane, and coupling constants are recorded in Hertz (Hz). Patterns are designated as s: singlet, d: doublet, t: triplet, q: quartet, m: multiplet, br: broad, br.s: broad singlet.

For the optical resolution of the compound, Parallex Flex™ produced by Biotage (column: one of CHIRAL-PAK® AD-H, IA, 11, and IC produced by DAICEL; and CHIRALCEL® OD-H and OJ-H produced by DAICEL) was used.

In the reactions using a microwave reactor in the Production Examples, Reference Examples, and Examples, Initiator™ or Initiator+ ™ produced by Biotage was used.

Regarding chromatography, as silica gel, Silica Gel60 produced by Merck (70-230 mesh or 230-400 mesh ASTM) or PSQ60B produced by Fuji Silysia Chemical Ltd. was used, or a pre-packed column {column: Hi-Flash™ Column (Silicagel) produced by YAMAZEN, size: one of S (16×60 mm), M (20×75 mm), L (26×100 mm), 2 L (26×150 mm), and 3 L (46×130 mm); or Biotage™ SNAP Ultra Silica Cartridge produced by Biotage, size: one of 10 g, 25 g, and 50 g} was used.

As NH silica gel, CHROMATOREX NH-DM2035 produced by Fuji Silysia Chemical Ltd. was used, or a pre-packed column {column: Hi-Flash™ Column (Amino) produced YAMAZEN, size: one of S (16×60 mm), M (20×75 mm), L (26×100 mm), 2 L (26×150 mm), and 3 L (46×130 mm); or Presep™ (Luer Lock) NH2(HC) produced by Wako Pure Chemical Industries, Ltd., size: one of type M (14 g/25 mL), type L (34 g/70 mL), type 2 L (50 g/100 mL), and type 3 L (110 g/200 mL)} was used.

As names of the compounds shown below, except for generally used reagents, those shown in the "E-Notebook" Version 12 (PerkinElmer) were used.

Production Example 1

Synthesis of ethyl 2-amino-6-methyl-4,5,6,7-tetrahydrothieno[2,3-c]pyridine-3-carboxylate

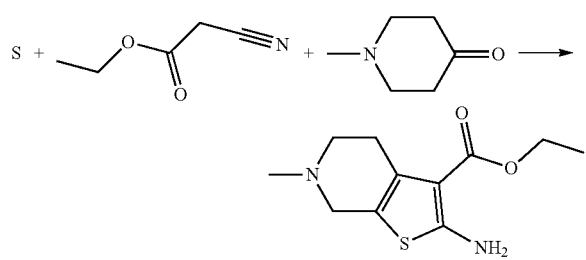

TEA (61.6 mL, 442 mmol) was added at room temperature to a mixture of 1-methyl-4-piperidone (CAS No. 1445-73-4) (51.5 mL, 442 mmol), ethyl cyanoacetate (CAS No. 105-56-6) (47.2 mL, 442 mmol), sulfur (CAS No. 7704-34-9) (14.2 g, 442 mmol), and ethanol (800 mL). The reaction mixture was stirred at 40° C. for 15 hours, and then concentrated under reduced pressure. The residue was purified by column chromatography (NH silica gel, ethyl acetate). The obtained concentrated residue was triturated with ethyl acetate. The precipitates were collected by filtration, washed with ethyl acetate, and dried under reduced pressure to yield the title compound (58.4 g).

$^1$H-NMR (400 MHz, CDCl$_3$) δ (ppm): 1.33 (t, J=7.0 Hz, 3H), 2.44 (s, 3H), 2.62-2.70 (m, 2H), 2.79-2.88 (m, 2H), 3.37 (t, J=2.0 Hz, 2H), 4.26 (q, J=7.3 Hz, 2H), 5.97 (br. s, 2H).

MS (ESI) m/z: 241 [M+H]$^+$

Production Example 2

Synthesis of 7-fluoro-4-methyl-3,4-dihydro-1H-benzo[e][1,4]diazepine-2,5-dione

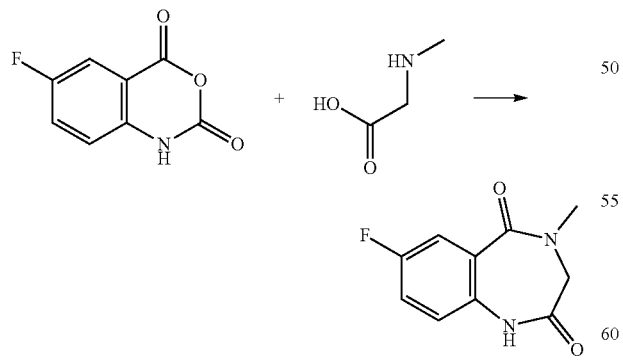

Sarcosine (CAS No. 107-97-1) (5.16 g, 58.0 mmol) was added at room temperature to a solution of 6-fluoro-1H-benzo[d][1,3]oxazine-2,4-dione (CAS No. 321-69-7) (10.0 g, 55.2 mmol) in pyridine (100 mL), and the reaction mixture was stirred at 100° C. for 8 hours. The reaction mixture was cooled to room temperature. The precipitates were collected by filtration and washed with diethyl ether. The obtained solid was dried under reduced pressure to yield the title compound (5.34 g).

$^1$H-NMR (400 MHz, CDCl$_3$) δ (ppm): 3.30 (s, 3H), 3.90 (s, 2H), 6.97 (dd, J 8.8, 4.5 Hz, 1H), 7.20 (ddd, J=8.6, 7.6, 2.9 Hz, 1H), 7.67 (dd, J=9.0, 3.1 Hz, 1H), 7.99 (br. s, 1H).

MS (ESI) m/z: 209 [M+H]$^+$

Production Example 3

Synthesis of 4-methyl-3,4-dihydro-1H-thieno[3,2-e][1,4]diazepine-2,5-dione

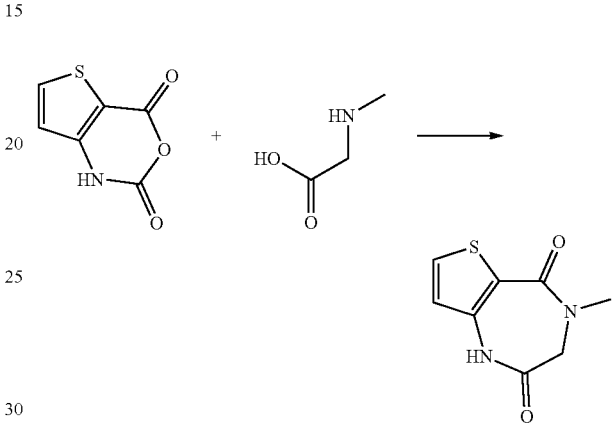

A mixture of 1H,2H,4H-thieno[3,2-d][1,3]oxazine-2,4-dione (CAS No. 78756-28-2) (300 mg, 1.77 mmol), sarcosine (395 mg, 4.43 mmol), and water (10 mL) was heated under reflux for 2 hours. The reaction mixture was cooled to 0° C. The precipitates was collected by filtration, and washed sequentially with water and diethyl ether. The obtained solid was dried under reduced pressure to yield the title compound (165 mg).

$^1$H-NMR (400 MHz, CDCl$_3$) δ (ppm): 3.24 (s, 3H), 4.00 (s, 2H), 6.72 (d, J=5.3 Hz, 1H), 7.52 (d, J=5.3 Hz, 1H), 7.96 (br. s, 1H).

MS (ESI) m/z: 197 [M+H]$^+$

Production Example 4

Synthesis of 4-methyl-3,4-dihydro-1H-thieno[2,3-e][1,4]diazepine-2,5-dione

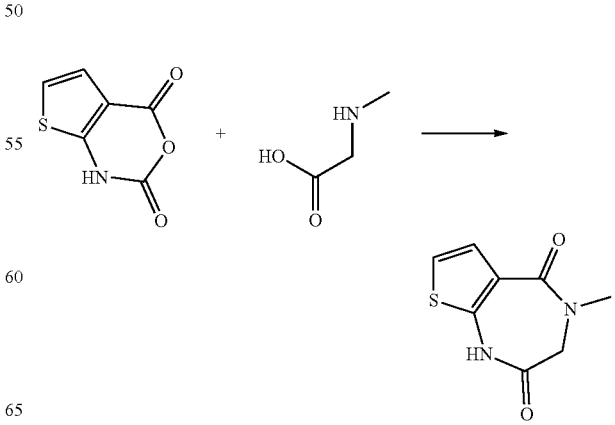

1H,2H,4H-thieno[2,3-d][1,3]oxazine-2,4-dione (CAS No. 103979-54-0) (600 mg, 3.55 mmol) was added to a solution of sarcosine (790 mg, 8.87 mmol) in water (12 mL). The reaction mixture was heated under reflux for 1.5 hours. The reaction mixture was cooled to room temperature. Chloroform was added to the reaction mixture, and the organic layer was separated. The aqueous layer was extracted with chloroform (twice) and ethyl acetate (3 times). The combined organic layer was dried over anhydrous sodium sulfate and filtered, and the filtrate was concentrated under reduced pressure. The obtained solid was dried to yield the title compound (430 mg).

$^{1}$H-NMR (400 MHz, CDCl$_3$) δ (ppm): 3.23 (s, 3H), 3.99 (s, 2H), 6.90 (d, J=5.9 Hz, 1H), 7.29 (d, J=5.7 Hz, 11H), 8.39 (br. s, 1H).

MS (ESI) m/z: 197 [M+H]$^+$

Production Example 5

Synthesis of (5aS,8aR)-4-methyloctahydrocyclopenta[e][1,4]diazepine-2,5-dione

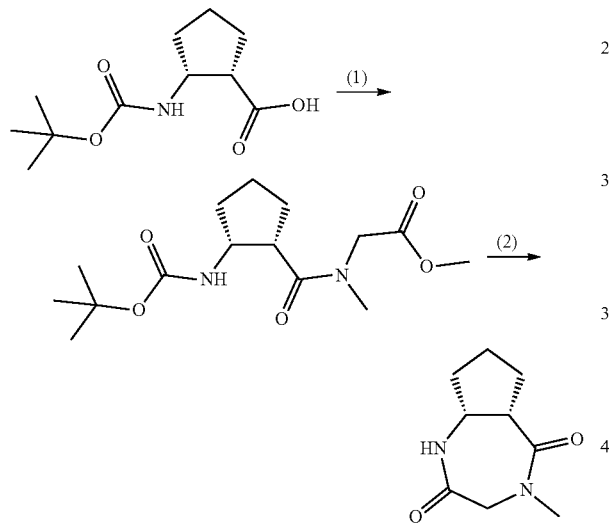

(1) Synthesis of methyl 2-((1S,2R)-2-((t-butoxycarbonyl)amino)-N-methylcyclopentanecarboxamide)acetate TEA (22.2 mL, 159 mmol), HOBT/monohydrate (11.7 g, 76.3 mmol), and EDC (14.6 g, 76.3 mmol) were sequentially added under ice cooling to a mixture of (1 S,2R)-2-((t-butoxycarbonyl)amino)cyclopentane-1-carboxylic acid (CAS No. 137170-89-9) (14.6 g, 63.6 mmol), sarcosine methyl ester hydrochloride (CAS No. 13515-93-0) (10.7 g, 76.3 mmol), and THF (150 mL). After the reaction mixture was stirred at room temperature for 15 hours, ethyl acetate and water were added, and the organic layer was separated. The aqueous layer was extracted with ethyl acetate. The combined organic layer was washed sequentially with a saturated sodium hydrogen carbonate aqueous solution and a saturated sodium chloride solution, dried over anhydrous sodium sulfate, filtered, and concentrated under reduced pressure. The obtained residue was purified twice by column chromatography (silica gel, 25-30% ethyl acetate/n-heptane) to yield the title compound (16.1 g).

MS (ESI) m/z: 337 [M+Na]$^+$ (2) Synthesis of (5aS,8aR)-4-methloctahydrocyclopenta[e][1,4]diazepine-2,5-dione A 4 N hydrogen chloride/1,4-dioxane solution (160 mL, 640 mmol) was added under ice cooling to methyl 2-((1S, 2R)-2-((t-butoxycarbonyl)amino)-N-methylcyclopentanecarboxamide)acetate (16.1 g, 51.3 mmol). The reaction mixture was stirred at the same temperature for 30 minutes, then stirred at room temperature for 45 minutes, and concentrated under reduced pressure. TBD (8.57 g, 61.6 mmol) was added under water cooling to a solution of the residue in methanol (130 ml). The reaction mixture was stirred under water cooling for 3 hours, and then cooled to 0° C. The resulting solid was collected by filtration, washed 3 times with ice-cooled methanol, and dried under reduced pressure to yield the title compound (5.22 g).

$^{1}$H-NMR (400 MHz, CDCl$_3$) δ (ppm): 1.41-1.59 (m, 2H), 1.78-1.98 (m, 2H), 2.00-2.15 (m, 1H), 2.36-2.53 (m, 1H), 3.08 (s, 3H), 3.18-3.32 (m, 1H), 3.49 (dd, J=15.5, 1.7 Hz, 1H), 3.91-4.04 (m, 1H), 4.51 (d, J=15.4 Hz, 1H), 5.54 (br. s, 1H).

MS (ESI) m/z: 183 [M+H]$^+$

Production Example 6

Synthesis of (5aR,8aR)-4-methyloctahydrocyclopenta[e][1,4]diazepine-2,5-dione

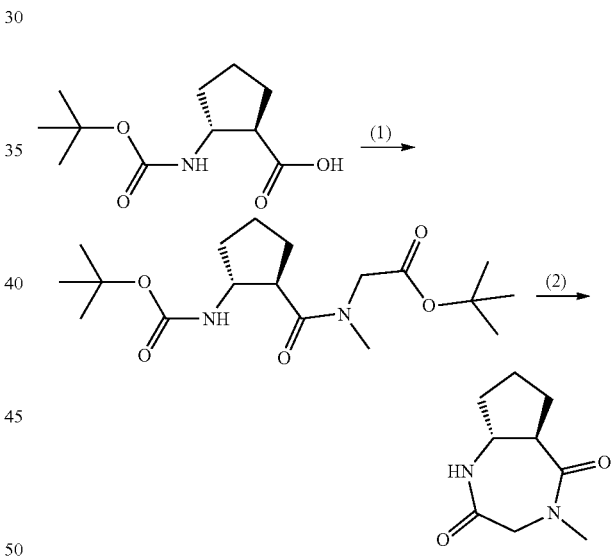

(1) Synthesis of t-butyl 2-((1R,2R)-2-((t-butoxycarbonyl)amino)-N-methylcyclopentanecarboxamide)acetate DIPEA (1.81 mL, 10.5 mmol) and HATU (1.99 g, 5.23 mmol) were sequentially added at room temperature to a mixture of (1R,2R)-t-butoxycarbonyl-2-aminocyclopentanecarboxylic acid (CAS No. 245115-25-7) (1.00 g, 4.36 mmol), sarcosine t-butyl ester hydrochloride (CAS No. 136088-69-2) (872 mg, 4.80 mmol), and DCM (10 mL). The reaction mixture was stirred at room temperature for 1 hour, and then directly purified by column chromatography (silica gel, 30-50% ethyl acetate/n-heptane) to yield the title compound (1.61 g).

MS (ESI) m/z: 357 [M+H]$^+$

(2) Synthesis of (5aR,8aR)-4-methyloctahydrocyclopenta[e][1,4]diazepine-2,5-dione A 4 N hydrogen chloride/1,4-dioxane solution (16 mL, 64 mmol) was added at room temperature to t-butyl 2-((1R, 2R)-2-((t-butoxycarbonyl)amino)-N-methylcyclopentanecarboxamide)acetate (1.61 g, 4.52 mmol), and the mixture was stirred for 20 hours. The reaction mixture was concentrated under reduced pressure. Sodium hydrogen carbonate (0.911 g, 10.8 mmol), methanol (24 mL), NMM (0.099 mL, 0.90 mmol), and DMT-MM (12.3% $H_2O$, 1.80 g, 5.70 mmol) were sequentially added to the residue at room temperature, and the mixture was stirred for 20 hours. The reaction mixture was concentrated under reduced pressure, and the residue was washed with DCM. The washed liquid was concentrated under reduced pressure, and the residue was purified by column chromatography (silica gel, 5-20% methanol/ethyl acetate) to yield the title compound (745 mg).

$^1$H-NMR (400 MHz, $CDCl_3$) δ (ppm): 1.56-1.88 (m, 3H), 1.91-2.02 (m, 1H), 2.13-2.23 (m, 1H), 2.26-2.39 (m, 1H), 3.07 (s, 3H), 3.08-3.16 (m, 1H), 3.51-3.62 (m, 1H), 3.79 (d, J=18.0 Hz, 1H), 4.58 (d, J=18.0 Hz, 1H), 6.76 (br. s, 1H).

MS (ESI) m/z: 183 [M+H]$^+$

Production Example 7

Synthesis of (5aS,8aS)-4-methyloctahydrocyclopenta[e][1,4]diazepine-2,5-dione

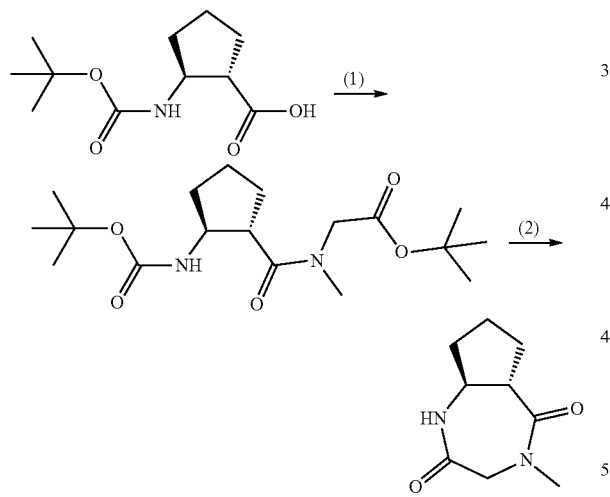

(1) Synthesis of t-butyl 2-((1 S,2S-2-((t-butoxycarbonyl)amino)-N-methylcyclopentanecarboxamide)acetate HATU (1.99 g 5.23 mmol) was added at room temperature to a mixture of (1S,2S)-t-butoxycarbonyl-2-aminocyclopentanecarboxylic acid (CAS No. 143679-80-5) (1.00 g, 4.36 mmol), sarcosine t-butyl ester hydrochloride (872 mg, 4.80 mmol), DIPEA (1.81 mL, 10.5 mmol), and DCM (10 mL). The reaction mixture was stirred at room temperature overnight, and then directly purified by column chromatography (silica gel, 30-50% ethyl acetate/n-heptane) to yield the title compound (1.55 g).

MS (ESI) m/z: 357 [M+H]$^+$

(2) Synthesis of (5aS,8aS)-4-methyloctahdrocclopentae][1,4]diazepine-2,5-dione A 4 N hydrogen chloride/1,4-dioxane solution (16 mL, 64 mmol) was added at room temperature to t-butyl 2-((1 S,2S)-2-((t-butoxycarbonyl)amino)-N-methylcyclopentanecarboxamide)acetate (1.55 g, 4.35 mmol), and the mixture was stirred for 16 hours. The reaction mixture was concentrated under reduced pressure. Sodium hydrogen carbonate (0.877 g, 10.4 mmol), methanol (24 mL), NMM (0.096 mL, 0.87 mmol), and DMT-MM (12.3% $H_2O$, 1.73 g, 5.48 mmol) were sequentially added to the residue at room temperature, and the mixture was stirred for 3 hours. The reaction mixture was concentrated under reduced pressure, and the residue was washed with DCM. The washed liquid was concentrated under reduced pressure, and the residue was purified by column chromatography (silica gel, 0-20% methanol/ethyl acetate) to yield the title compound (753 mg).

$^1$H-NMR (400 MHz, $CDCl_3$) δ (ppm): 1.55-1.88 (m, 3H), 1.91-2.02 (m, 1H), 2.11-2.22 (m, 1H), 2.25-2.40 (m, 1H), 3.07 (s, 3H), 3.07-3.16 (m, 1H), 3.51-3.62 (m, 1H), 3.78 (d, J=18.0 Hz, 1H), 4.57 (d, J=18.0 Hz, 1H), 6.54 (br. s, 1H).

MS (ESI) m/z: 183 [M+H]$^+$

Example 1

Synthesis of 3-fluoro-6,11-dimethyl-6,7,10,11,12,13-hexahydrobenzo[f]pyrido[4",3":4',5']thieno[2',3':4,5]pyrimido 1,2-a][1,4]diazepine-5,14-dione

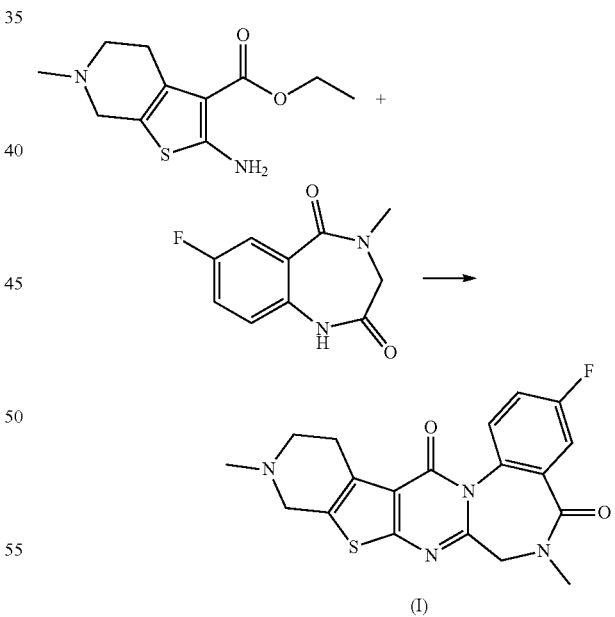

Phosphorus oxychloride (4.65 mL, 49.9 mmol) was added at room temperature to a mixture of ethyl 2-amino-6-methyl-4,5,6,7-tetrahydrothieno[2,3-c]pyridine-3-carboxylate (6.00 g, 25.0 mmol) obtained in Production Example 1, 7-fluoro-4-methyl-3,4-dihydro-1H-benzo[e][1,4]diazepine-2,5-dione (5.20 g, 25.0 mmol) obtained in Production Example 2, and DCE (300 mL). The reaction mixture was stirred at 80° C. for 20 hours. While stirring under ice-cooling, sodium ethoxide (a 20% solution in ethanol, 80 mL, 207 mmol) was added to the reaction mixture. The reaction mixture was stirred at room temperature for 20 minutes. A saturated sodium hydrogen carbonate aqueous solution and ethyl acetate were added to the reaction mixture, and the organic layer was separated. The aqueous layer was extracted with ethyl acetate. The combined organic layer was dried over magnesium sulfate and filtered, and the filtrate was concentrated under reduced pressure. The residue was sequentially purified by column chromatography (NH silica gel, 50-100% ethyl acetate/n-heptane) and column chromatography (silica gel, 0-50% methanol/ethyl acetate). The obtained solid was triturated with TBME, and the precipitates were collected by filtration. The obtained solid was washed with TBME and dried under reduced pressure to yield the title compound (4.56 g).

$^1$H-NMR (400 MHz, CDCl$_3$) δ (ppm): 2.51 (s, 3H), 2.66-2.76 (m, 1H), 2.77-2.88 (m, 1H), 3.04-3.18 (m, 2H), 3.25 (s, 3H), 3.57-3.75 (m, 2H), 4.09 (d, J 15.2 Hz, 1H), 4.47 (d, J=14.8 Hz, 1H), 7.25-7.31 (m, 1H), 7.60-7.64 (m, 1H), 7.67 (dd, J=9.0, 4.7 Hz, 1H).

MS (ESI) m/z: 385 [M+H]$^+$

Example 2

Synthesis of 5,10-dimethyl-5,6,9,10,11,12-hexahydropyrido[4'',3'':4',5']thieno[2',3':4,5]pyrimido[1,2-a]thieno[2,3-f][1,4]diazepine-4,13-dione

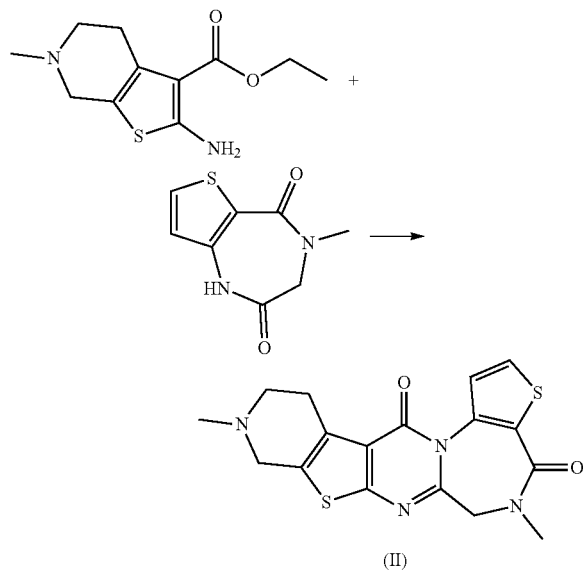

(II)

Phosphorus oxychloride (0.157 mL, 1.68 mmol) was added at room temperature to a mixture of ethyl 2-amino-6-methyl-4,5,6,7-tetrahydrothieno[2,3-c]pyridine-3-carboxylate (303 mg, 1.26 mmol) obtained in Production Example 1, 4-methyl-3,4-dihydro-1H-thieno[3,2-e][1,4]diazepine-2,5-dione (165 mg, 0.841 mmol) obtained in Production Example 3, and 1,4-dioxane (10 mL). The reaction mixture was stirred at 70° C. for 2 hours, and then stirred at 90° C. for 5 hours. Sodium ethoxide (a 20% solution in ethanol, 2.60 mL, 6.73 mmol) was added to the reaction mixture cooled to room temperature. The reaction mixture was stirred at room temperature for 40 minutes. Ethyl acetate and a saturated sodium hydrogen carbonate aqueous solution were added to the reaction mixture, and the organic layer was separated. The aqueous layer was extracted with ethyl acetate. The combined organic layer was dried over anhydrous sodium sulfate, filtered, and concentrated under reduced pressure. The residue was purified by column chromatography (silica gel, 50% methanol/ethyl acetate) to yield the title compound (90.0 mg).

$^1$H-NMR (400 MHz, CDCl$_3$) δ (ppm): 2.51 (s, 3H), 2.66-2.87 (m, 2H), 3.07-3.20 (m, 2H), 3.26 (s, 3H), 3.56-3.74 (m, 2H), 4.21 (d, J=15.0 Hz, 1H), 4.56 (d, J=15.0 Hz, 1H), 7.54 (d, J=5.3 Hz, 1H), 7.59 (d, J=5.3 Hz, 1H).

MS (ESI) m/z: 373 [M+H]$^+$

Example 3

Synthesis of 5,10-dimethyl-5,6,9,10,11,12-hexahydropyrido[4'',3'':4',5']thieno[2',3':4,5]pyrimido[1,2-a]thieno[3,2-f][1,4]diazepine-4,13-dione

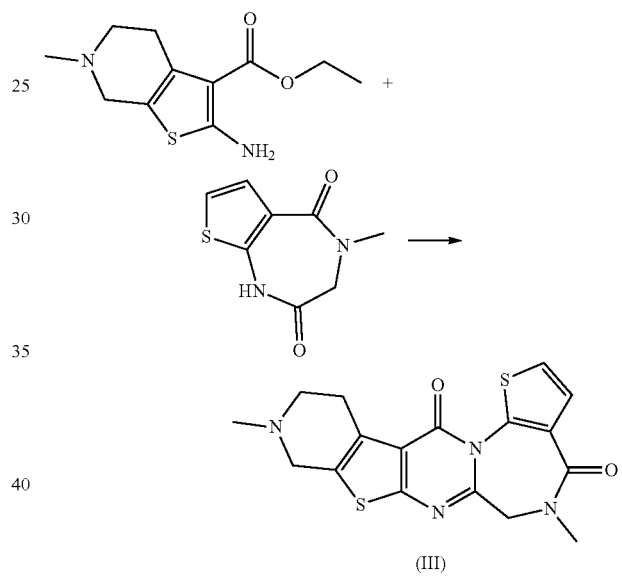

(III)

Phosphorus oxychloride (1.43 mL, 15.3 mmol) was added at room temperature to a mixture of 4-methyl-3,4-dihydro-1H-thieno[2,3-e][1,4]diazepine-2,5-dione (1.00 g, 5.10 mmol) obtained in Production Example 4, ethyl 2-amino-6-methyl-4,5,6,7-tetrahydrothieno[2,3-c]pyridine-3-carboxylate (1.84 g, 7.64 mmol) obtained in Production Example 1, and 1,4-dioxane (30 mL). The reaction mixture was stirred at room temperature for 5 minutes, and stirred at 90° C. for 2 hours. Sodium ethoxide (a 20% solution in ethanol, 21.7 mL, 56.1 mmol) was added over 5 minutes to the reaction mixture cooled to room temperature. The reaction mixture was stirred at room temperature for 1.5 hours. Ethyl acetate, a saturated sodium hydrogen carbonate aqueous solution, and water were sequentially added to the reaction mixture, and the organic layer was separated. The aqueous layer was extracted with ethyl acetate. The combined organic layer was dried over anhydrous magnesium sulfate and filtered, and the filtrate was concentrated under reduced pressure. The residue was purified by column chromatography (silica gel, 20%-50% methanol/ethyl acetate). The obtained solid was triturated with ethanol, and the precipitates were collected by filtration. The obtained solid was washed with ethanol, and dried under reduced pressure to yield the title compound (712 mg).

$^1$H-NMR (400 MHz, CDCl$_3$) δ (ppm): 2.52 (s, 3H), 2.71-2.87 (m, 2H), 3.05-3.30 (m, 5H), 3.59-3.75 (m, 2H), 4.23 (d, J=14.8 Hz, 1H), 4.57 (d, J=14.8 Hz, 1H), 7.35 (d, J=6.2 Hz, 1H), 7.39 (d, J=5.9 Hz, 1H).

MS (ESI) m/z: 373 [M+H]$^+$

Example 4

Synthesis of (3aS,14aR)-5,10-dimethyl-3,3a,5,6,9,10,11,12-octahydro-1H-cyclopenta[f]pyrido[4",3":4',5']thieno[2',3':4,5]pyrimido[1,2-a][1,4]diazepine-4,13(2H,14aH)-dione

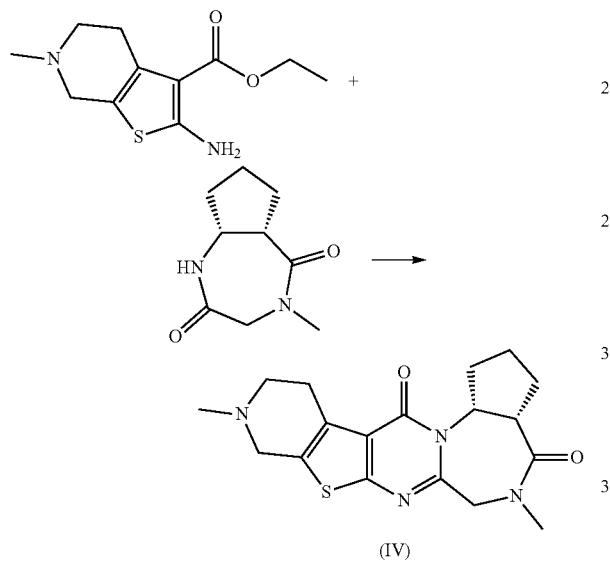

(IV)

Phosphorus oxychloride (7.93 mL, 85.1 mmol) was added at room temperature to a mixture of (5aS,8aR)-4-methyloctahydrocyclopenta[e][1,4]diazepine-2,5-dione (3.10 g, 17.0 mmol) obtained in Production Example 5-(2), ethyl 2-amino-6-methyl-4,5,6,7-tetrahydrothieno[2,3-c]pyridine-3-carboxylate (8.18 g, 34.0 mmol) obtained in Production Example 1, and DCE (300 mL). The reaction mixture was stirred at 80° C. for 14.5 hours. A saturated sodium hydrogen carbonate aqueous solution was added to the reaction mixture at 0° C., the mixture was stirred at room temperature for 3.5 hours, and then the organic layer was separated. The aqueous layer was extracted with ethyl acetate. The combined organic layer was washed sequentially with a saturated sodium hydrogen carbonate aqueous solution and a saturated sodium chloride solution, dried over anhydrous magnesium sulfate, filtered, and concentrated under reduced pressure. The residue was purified by column chromatography (NH silica gel, 30-60% ethyl acetate/n-heptane). The obtained concentrated residue was triturated with TBME, and the precipitates were collected by filtration. The obtained solid was washed 3 times with TBME, and dried under reduced pressure to yield the title compound (3.70 g).

$^1$H-NMR (400 MHz, CDCl$_3$) δ (ppm): 1.51-1.73 (m, 2H), 1.94-2.18 (m, 21H), 2.30-2.41 (m, 1H), 2.44-2.59 (m, 4H), 2.71-2.82 (m, 2H), 3.04-3.19 (m, 5H), 3.42-3.54 (m, 1H), 3.64 (s, 2H), 4.17 (d, J=15.6 Hz, 1H), 4.75 (d, J=15.6 Hz, 1H), 5.69-5.82 (m, 1H-1).

MS (ESI) m/z: 359 [M+H]$^+$

Specific rotation: $[\alpha]_D^{20}$-146.0 (c 0.50, CHCl$_3$)

Analysis by HPLC:

(Analysis conditions) Column: CHIRALPAK IB (produced by Daicel Chemical Industries, Ltd.) (0.46 cm φ×15 cm), 40° C., eluent: ethanol/hexane=20/80 (v/v), flow rate: 1 ml/min., detection: UV (254 nm).

(Analysis results) When the title compound was analyzed under the above analysis conditions, the retention time was 10.38 minutes, the optical purity was >98% ee, and the optical rotation was (−). The retention time of the enantiomer was confirmed by the product synthesized similarly using a racemic mixture as a starting material.

Example 5

Synthesis of (3aR,14aR)-5,10-dimethyl-3,3a,5,6,9,10,11,12-octahydro-1H-cyclopenta[f]pyrido[4",3":4'5']thieno[2',3':4,5]pyrimido[1,2-a][1,4]diazepine-4,13(2H,14aH)-dione

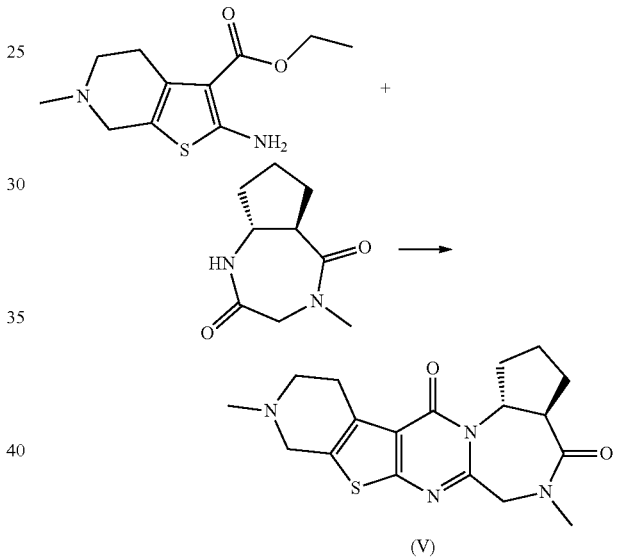

(V)

Phosphorus oxychloride (0.793 mL, 8.51 mmol) was added at room temperature to a mixture of (5aR,8aR)-4-methyloctahydrocyclopenta[e][1,4]diazepine-2,5-dione (310 mg, 1.70 mmol) obtained in Production Example 6-(2), ethyl 2-amino-6-methyl-4,5,6,7-tetrahydrothieno[2,3-c]pyridine-3-carboxylate (613 mg, 2.55 mmol) obtained in Production Example 1, and DCE (16 mL). The reaction mixture was stirred at 70° C. for 2.5 hours and then returned to room temperature, and ethyl acetate (15 mL) and a saturated sodium hydrogen carbonate aqueous solution (30 mL) were added. The reaction mixture was stirred at room temperature for 5 days, ethyl acetate was added, and the organic layer was separated. The aqueous layer was extracted with ethyl acetate. The combined organic layer was dried over anhydrous sodium sulfate, filtered, and concentrated under reduced pressure. The residue was purified by column chromatography (NH silica gel, 50-70% ethyl acetate/n-heptane). The obtained product was washed 3 times with diethyl ether, then washed with TBME, and dried under reduced pressure to yield the title compound (143 mg).

¹H-NMR (400 MHz, CDCl₃) δ (ppm): 1.29-1.49 (m, 1H), 1.68-1.83 (m, 1H), 1.82-2.21 (m, 3H), 2.50 (s, 3H), 2.76 (t, J=5.7 Hz, 2H), 2.98-3.23 (m, 6H), 3.40-3.54 (m, 1H), 3.57-3.68 (m, 2H), 4.17-4.34 (m, 2H), 5.30 (d, J=17.4 Hz, 1H).

MS (ESI) m/z: 359 [M+H]⁺

Analysis by HPLC:

(Analysis conditions) Column: CHIRALPAK IC (produced by Daicel Chemical Industries, Ltd.) (0.46 cm (p×15 cm), 40° C., eluent: ethanol, flow rate: 1 mL/min., detection: UV (254 nm)

(Analysis results) The retention time of the title compound was 6.64 minutes, the optical purity was >99% ee, and the optical rotation was (−).

Example 6

Synthesis of (3aS,14aS)-5,10-dimethyl-3,3a,5,6,9,10,11,12-octahydro-H-cyclopenta[f]pyrido[4″,3″:4′,5′]thieno[2′,3′:4,5]pyrimido[1,2-a][1,4]diazepine-4,13(2H,14aH)-dione

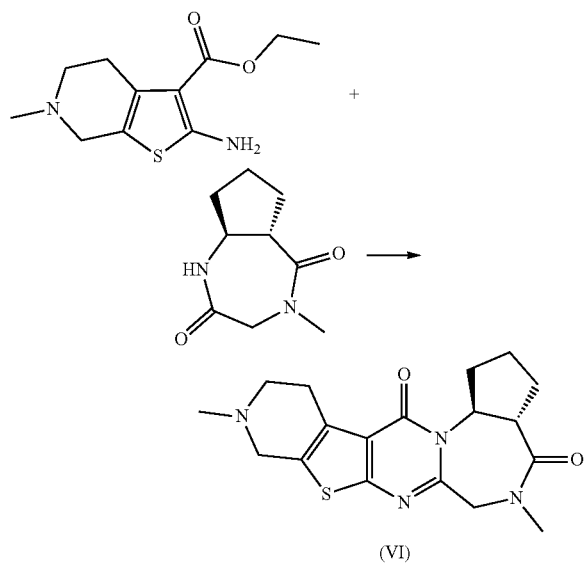

Phosphorus oxychloride (0.859 mL, 9.22 mmol) was added at room temperature to a mixture of (5aS,8aS)-4-methyloctahydrocyclopenta[e][1,4]diazepine-2,5-dione (336 mg, 1.84 mmol) obtained in Production Example 7-(2), ethyl 2-amino-6-methyl-4,5,6,7-tetrahydrothieno[2,3-c]pyridine-3-carboxylate (665 mg, 2.77 mmol) obtained in Production Example 1, and DCE (17 mL). The reaction mixture was stirred at 60° C. for 3.5 hours, and then returned to room temperature. Ethyl acetate (15 mL) and a saturated sodium hydrogen carbonate aqueous solution (30 mL) were added to the reaction mixture. After the reaction mixture was stirred at room temperature for 5 days, ethyl acetate was added, and the organic layer was separated. The aqueous layer was extracted with ethyl acetate. The combined organic layer was dried over anhydrous sodium sulfate, filtered, and concentrated under reduced pressure. The residue was purified by column chromatography (NH silica gel, 40-80% ethyl acetate/n-heptane). The obtained product was washed 3 times with diethyl ether and dried under reduced pressure to yield the title compound (166 mg).

¹H-NMR (400 MHz, CDCl₃) δ (ppm): 1.31-1.50 (m, 1H), 1.69-1.83 (m, 1H), 1.84-1.97 (m, 1H), 1.97-2.20 (m, 2H), 2.50 (s, 3H), 2.73-2.80 (m, 2H), 3.02-3.23 (m, 6H), 3.41-3.55 (m, 1H), 3.57-3.69 (m, 2H), 4.19-4.34 (m, 2H), 5.30 (d, J=17.2 Hz, 1H).

MS (ESI) m/z: 359 [M+H]⁺

(Analysis conditions) Column: CHIRALPAK IC (produced by Daicel Chemical Industries, Ltd.) (0.46 cm φ×15 cm), 40° C., eluent: ethanol, flow rate: 1 mL/min., detection: UV (254 nm)

(Analysis results) The retention time of the title compound was 8.34 minutes, the optical purity was >99% ee, and the optical rotation was (+).

Pharmacological Test Examples

The following pharmacological tests were conducted using the compounds of Examples 1 to 6.

Measurement of acetylcholine (ACh) release in the rat primary septal neuron culture system in the presence of NGF (1) Rat Primary Septal Neuron Culture The septal area was isolated from Sprague-Dawley (SD) rats (Charles River Laboratories Japan, Inc.) at a fetal age of 18 days, and cultured.

Specifically, fetuses were aseptically removed from pregnant rats under isoflurane anesthesia. The brain was extracted from each fetus, and immersed in ice-cooled L-15 medium (11415-064, Thermo Fisher Scientific). The septal area was dissected from the extracted brain under a stereoscopic microscope. The dissected septal area was subjected to enzyme treatment in an enzyme solution containing 0.25% trypsin (15050-065, Thermo Fisher Scientific) and 0.01% DNase (D5025-150KU, Sigma) at 37° C. for 30 minutes, thereby dispersing the cells. In this case, the enzyme reaction was terminated by adding inactivated horse serum (26050-088, Thermo Fisher Scientific). The enzyme-treated solution was centrifuged at 1000 rpm for 3 minutes, and the supernatant was removed. A medium in an amount of 10 mL was added to the obtained cell mass. The medium used was Dulbecco's Modified Eagle's Medium (044-29765, WAKO) supplemented with N2 supplement (17502-048, Thermo Fisher Scientific), 1 mM sodium pyruvate (11360-070, Thermo Fisher Scientific), and Penicillin-Streptomycin (15140-1221, Thermo Fisher Scientific). The cells of the cell mass to which the medium was added were redispersed by gentle pipetting, and then centrifuged again at 1000 rpm for 3 minutes, and the supernatant was removed. The medium in an amount of 10 mL was added to the obtained cell mass, and the cell dispersion was filtered through a 40-μm nylon mesh (Cell Strainer) to remove the cell mass, thereby obtaining a neuronal cell suspension. The neuronal cell suspension was diluted with the medium, and 10% inactivated bovine serum (26140-079, Thermo Fisher Scientific) and 10% inactivated horse serum were added. Thereafter, 100 μL/well of the suspension was seeded in a 96-well plate (354461, CORNING) pre-coated with poly-D-lysine so that the initial culture density was 1.4×10⁵ cells/cm². After the seeded cells were cultured under 5% CO₂-95% air in a 37° C. incubator for 2 days, the entire medium was replaced with 120 μL of fresh medium, and the cells were subsequently cultured for 5 days.

(2) Compound Addition

On the 7th day of culture, compound was added in the following manner. A solution of the test compound in DMSO was diluted with the medium so that the concentration was 10 times higher than the final concentration. NGF (450-01, PEPRO TECH, INC.) was prepared at 0.3 ng/mL.

These two solutions were added each in an amount of 15 µL/well, and the mixture was mixed well. The final DMSO concentration was 0.1% or less. Moreover, only DMSO and NGF were added to the control group.

(3) ACh Release Measurement

One day after compound addition, an amount of ACh release was measured by HPLC in the following manner. A warmed buffer was added at 100 µL/well to the well after the medium was eliminated, and the buffer was immediately removed. Thereafter, a buffer to which 10 µm choline, 10 µm physostigmine, and 6 mM KCl were added was added at 120 µL/well. The buffer was prepared by adding 125 mM NaCl, 25 mM 4-(2-hydroxyethyl)-1-piperazineethanesulfonic acid, 1.2 mM $KH_2PO_4$, 1.2 mM $MgSO_4$, 2.2 mM $CaCl_2$ ($2H_2O$), and 10 mM glucose to sterilized water, and the final pH of the solution was set to 7.4. After the 96-well plate to which the buffer was added was incubated under 5% $CO_2$-95% air in a 37° C. incubator for 40 minutes, 80 µL of buffer was collected. An internal standard solution IPHC ($5 \times 10^{-7}$ M) was added in an amount of 6 µL to the collected buffer, and the buffer was transferred to a tube for HPLC measurement and subjected to HPLC measurement. The results are represented by the effect of each compound as the percentage (% of control) of the ACh concentration in the buffer of the control group, and the compound concentrations showing a 20% increase from the ACh concentration in the buffer of the control group are shown in the following Table 1.

TABLE 1

| Example | Concentration (µM) showing a 20% or more increase from the amount of ACh in the control group |
|---|---|
| 1 | 0.1 |
| 2 | 0.1 |
| 3 | 0.1 |
| 4 | 0.1 |
| 5 | 0.1 |
| 6 | 0.03 |

Measurement of Choline Acetyltransferase (ChAT) mRNA Expression Levels in the Rat Septal Area (1) Compound Administration In this study, SD male rats (Charles River Laboratories Japan, Inc.) with a body weight of about 250 to 350 g were used. The compound was dissolved in 0.01 mol/L hydrochloric acid, and orally administered.

(2) Sampling

At 24 hours after the administration of the compound, the whole brain tissue was collected under pentobarbital anesthesia. The medial septum was isolated from whole brain on ice and frozen with liquid nitrogen, and then stored at −80° C.

(3) Measurement of ChAT mRNA Expression Levels

For RNA purification, RNeasy Plus Mini Kit (#74136: QIAGEN) was used in this study. RNA purification was performed by the method described in the kit. After RNA purification, the total RNA concentration was measured by using QIAxpert Instrument (QIAGEN). cDNA was synthesized using SuperScript® VILO™ cDNA Synthesis Kit (#11754: Thermo Fisher Scientific). The synthesis of cDNA was performed by the method described in the kit. The synthesized cDNA was diluted 4 times with RNase free water, and the diluted cDNA solution was used as a sample. Taqman Universal PCR Master Mix (#4304437: Thermo Fisher Scientific), Taqman® Gene Expression Assays, INVENTORIED (#4331182: Thermo Fisher Scientific), RNase free water, and the cDNA solution were mixed in amounts of 10 µl, 1 µl, 4 µl, and 5 µl, respectively, and the resulting mixture was used as a measurement sample solution. Quantitative polymerase chain reaction (qPCR) was conducted using ABI PRISM® 7900HT (Thermo Fisher Scientific) by a fluorescence probe method. Analysis was performed by SDS 2.4 (Thermo Fisher Scientific). The results were calculated by the percentage of the amount of ChAT mRNA expression levels in the compound administration group increased from the amount of ChAT mRNA expression levels in the vehicle administration group. The results are shown in the following Table 2.

TABLE 2

| Example | Dose | Amount (%) increased from the amount of ChAT mRNA expression levels in the vehicle administration group |
|---|---|---|
| 1 | 10 mg/kg | 73.3 |
| 2 | 3 mg/kg | 38.0 |
| 3 | 10 mg/kg | 56.4 |
| 4 | 10 mg/kg | 42.4 |
| 5 | 3 mg/kg | 33.6 |
| 6 | 10 mg/kg | 32.0 |

Measurement of Acetylcholine (ACh) in Rat Cerebrospinal Fluid (CSF)

(1) Background

Correlation between increase and decrease of intracerebral neurotransmitters and those in cerebrospinal fluid (CSF) was revealed by studies on rodents and the correlation was also seen in human (Lowe S et al. Psychopharmacology 219 (2012) 959-970). Thus, the changes in acetylcholine in CSF were measured in order to determine the changes in intracerebral acetylcholine by the test compounds.

(2) Compound Administration

In this study, Fischer344 male rats (Charles River Laboratories Japan, Inc.) with a body weight of about 150 to 250 g were used. The test compounds were orally administered to the rats once a day at 10 mg/kg for three days. The vehicle used was 0.01 mol/L hydrochloric acid.

(3) Sampling

At 24 hours after the administration of the vehicle and the test compounds, the CSF was collected from cistema magna in a tube containing AchE inhibitors under pentobarbital anesthesia. The collected CSF was centrifuged at 3500×g at 4° C. for 10 minutes and the supernatant was collected. The collected supernatant was frozen with liquid nitrogen, and then stored at −80° C.

(4) Measurement of Ach by LC-MS

To 10 µL of the CSF was added 50 µL of acetylcholine-d9 chloride (ACh-d9) at a final concentration of 0.34 nmol/L as an internal standard. The mixture was pipetted and centrifuged at 1500×g at 4° C. for 10 minutes. The supernatant was collected and subjected to LC/MS (NexeraX2 (MS), TSQ Altis (HPLC)), and Ach was detected as precursor ion at m/z 146.050 and as product ion at m/z 87.071 and ACh-d9 as an internal standard was detected as precursor ion at m/z 155.088 and as product ion at m/z 87.000. The results were shown as calculations of a percentage of increase in ACh concentration in CSF in the test compound administration group with respect to that in vehicle administration group (% of control). The results were shown in Table 3.

TABLE 3

| Example | Amount (%) increased with respect to from the amount of ACh in CSF the vehicle administration group |
|---|---|
| 1 | 160.0 |
| 3 | 156.8 |

Evaluation in Human Tau P301S Transgenic Mouse
(1) Compound Administration

In this study, the test compounds were orally administered to human tau P301S transgenic mice once a day for three months from four-month-old to seven-month-old. The vehicle used was 0.01 mol/L hydrochloric acid.
(2) Sampling At the initial day of the administration (four-month-old) and at the next day of the final administration, mice of vehicle administration group and test compound administration group were anesthetized under pentobarbital (50 mg/kg, i.p.) and perfused with PBS. After the perfusion, the forebrain including the medial septal area was collected and fixed with 4% paraformaldehyde.
(3) Preparation of Brain Coronal Frozen Section The collected forebrain including the medial septal area was immersed and shaken overnight in 4% paraformaldehyde. The immersion solution was replaced with 7.5% sucrose solution. It was immersed and shaken overnight in 7.5% sucrose solution, and the immersion solution was replaced with 15% sucrose solution and it was immersed and shaken overnight. The immersion solution was replaced with 30% sucrose solution and it was immersed and shaken overnight. Brain coronal frozen sections with 30 μm thickness were prepared from the forebrain including the medial septal area by using a microtome (Leica, SM2000R).
(4) Immunohistochemistry of Choline Acetyltransferase (ChAT) Positive Cells The prepared brain coronal frozen sections were stained with DAB (DAB PEROXIDASE SUBSTRATE KIT (Vector, SK-4100)) using a ChAT antibody (Santa Cruz, S.C.-20672) as a primary antibody. The section image including the medial septal area as shown in "The mouse Brain in stereotaxic coordinates" (COMPACT THIRD EDITION, Keith B.J. Franklin & George Paxinos) was taken by an all-in-one fluorescence microscope (KEYENCE, BZ-X710) and ChAT positive cells around the major axis of the medial septal area were counted by BZ analysis software (KEYENCE). The results were shown as a percentage of the number of ChAT positive cells in the vehicle administration group and the test compound administration group with respect to the number of ChAT positive cells at the time of initial administration (four-month-old). Data are expressed as the mean±SEM. The differences between the group at the time of initial administration and the vehicle-treated group (significant: *) was analyzed by an unpaired t-test, and also the differences between the vehicle-treated group and compound-treated group (significant: #) was analyzed by unpaired t-test. A value of P<0.05 was considered statistically significant. Statistical analyses were performed using the GraphPad Prism version 7.02. The results were shown in Table 4.

TABLE 4

| Treatment Group | Ratio (%) of number of ChAT positive cells compared to that in the initial administration |
|---|---|
| Group at the time of initial administration | 100.0 ± 4.5 |
| Vehicle administration group | 83.0 ± 5.8* |
| Example 1 administration group (Dose: 10 mg/kg) | 105.0 ± 4.0[#] |
| Example 3 administration group (Dose: 5 mg/kg) | 105.3 ± 4.3[#] |

Neuroprotective and Restorative Effect on Cholinergic Neurons Usi Ng Fimbria-Fomix Lesioned Rat Model
(1) Preparation of Fimbria-Fomix Lesioned Rat Model In this study, Sprague-Dawley male rats (Charles River Laboratories Japan, Inc.) with a body weight of about 250 to 350 g were used. The rat was anesthetized under the combination of three drugs: midazolam (2 mg/kg s.c.), medetomidine hydrochloride (0.15 mg/kg s.c.) and butorphanol tartrate (2.5 mg/kg s.c.) and fixed with a brain stereotaxis apparatus (Narishige Co., Ltd.). The cranial was exposed and a hole with 5 mm width was drilled in the skull from the median line 2 mm posterior to Bregma. A razor with 4 mm width was pierced into the Bregma in 5.5 mm depth to cut fimbria-fornmix. After hemostasis, the scalp was sutured. After the operation, the rat was brought back to the cage and recovered from the anesthesia. In the sham-operated group, a hole with 5 mm width was drilled in the skull from the median line 2 mm posterior to Bregma, but no razor was pierced.
(2) Compound Administration The test compounds were orally administered to the rats once a day from five days to nine days after the operation (Example 1: 10 mg/kg) or from seven days to fourteen days after the operation (Example 3: 3 mg/kg). The vehicle used was 0.01 mol/L hydrochloric acid. In the sham-operated group, the vehicle was orally administered once a day similarly to the test compound administration group.
(3) Sampling The rats were anesthetized under pentobarbital and transcardially perfused with ice-cold PBS. After the perfusion, the forebrain including the medial septal area was collected and immersed and shaken overnight with 4% paraformaldehyde. The immersion solution was replaced with 7.5% sucrose solution. It was immersed and shaken overnight in 7.5% sucrose solution, and the immersion solution was replaced with 15% sucrose solution and it was immersed and shaken overnight. The immersion solution was replaced with 30% sucrose solution and it was immersed and shaken overnight. Brain coronal frozen sections with 30 μm thickness were prepared from the forebrain including the medial septal area by using a microtome (Leica, SM2000R).
(4) Immunohistochemistry of Choline Acetyltransferase (ChAT) Positive Cells and Vesicular Acetylcholine Transporter (VAChT)

The prepared brain coronal frozen sections were stained with DAB (DAB PEROXIDASE SUBSTRATE KIT (Vector, SK-4100)) using a ChAT antibody (Santa Cruz, S.C.-20672) or a VAChT antibody (Merck Millipore, ABN100) as a primary antibody. The section image including the medial septal area or hippocampus as shown in "The mouse Brain in stereotaxic coordinates" (COMPACT THIRD EDITION, Keith B.J. Franklin & George Paxinos) was taken by an all-in-one fluorescence microscope (KEYENCE, BZ-X710) and ChAT positive cells of the medial septal area or optical density (OD) in hippocampal VAChT were measured by BZ analysis software (KEYENCE). The results were shown as a percentage of the number of ChAT positive cells of the medial septal area or OD in hippocampal VAChT in the vehicle administration group and the test compound administration group with respect to the number of ChAT positive cells of the medial septal area or OD in hippocampal VAChT in the sham-operated group. Data are expressed as the mean±SEM. The differences between the vehicle-treated group and compound-treated (significant: #) was analyzed by unpaired t-test. A value of P<0.05 was considered statistically significant. Statistical analyses were performed using the GraphPad Prism version 7.02. The results were shown in Tables 5 and 6.

TABLE 5

| Example | Number of ChAT positive cells (%) at initial administration | Number of ChAT positive cells (%) in vehicle administration group | Number of ChAT positive cells (%) in test compound administration group |
|---|---|---|---|
| 1 | 59.9 ± 16.0 | 43.3 ± 12.3 | 79.1 ± 15.7 |
| 3 | 57.0 ± 17.5 | 38.4 ± 5.0 | 74.1 ± 9.3# |

TABLE 6

| Example | OD in hippocampal VAChT (%) at initial administration | OD in hippocampal VAChT (%) in vehicle administration group | OD in hippocampal VAChT (%) in test compound administration group |
|---|---|---|---|
| 1 | 35.4 ± 4.4 | 22.8 ± 9.5 | 77.1 ± 14.6# |
| 3 | 51.7 ± 13.1 | 19.5 ± 6.4 | 66.1 ± 14.2# |

What is claimed is:
1. A compound selected from the group consisting of:
3-fluoro-6,11-dimethyl-6,7,10,11,12,13-hexahydrobenzo[f]pyrido[4",3":4',5']thieno[2',3':4,5]pyrimido[1,2-a][1,4]diazepine-5,14-dione:

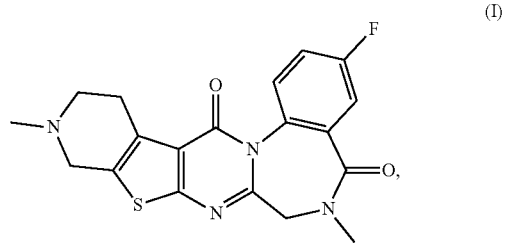 [SMILES: CN1CCc2c(sc3nc4n(c(=O)c23)-c2ccc(F)cc2C(=O)N(C)C4)C1]

(I)

5,10-dimethyl-5,6,9,10,11,12-hexahydropyrido[4",3":4',5']thieno[2',3':4,5]pyrimido[1,2-a]thieno[2,3-f][1,4]diazepine-4,13-dione:

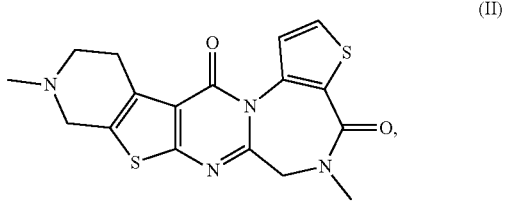 [SMILES: CN1CCc2c(sc3nc4n(c(=O)c23)-c2ccsc2C(=O)N(C)C4)C1]

(II)

5,10-dimethyl-5,6,9,10,11,12-hexahydropyrido[4",3":4',5']thieno[2',3':4,5]pyrimido[1,2-a]thieno[3,2-][1,4]diazepine-4,13-dione:

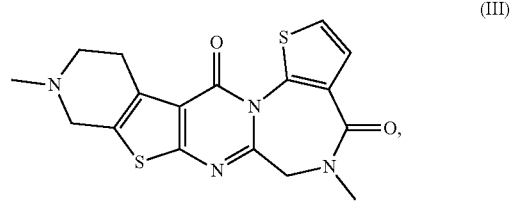 [SMILES: CN1CCc2c(sc3nc4n(c(=O)c23)-c2sccc2C(=O)N(C)C4)C1]

(III)

(3aS,14aR)-5,10-dimethyl-3,3a,5,6,9,10,11,12-octahydro-1H-cyclopenta[f]pyrido[4",3":4',5']thieno[2',3':4,5]pyrimido[1,2-a][1,4]diazepine-4,13(2H,14aH)-dione:

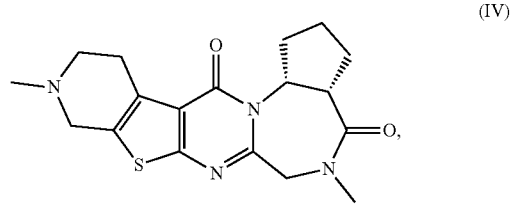 [SMILES: CN1CCc2c(sc3nc4n(c(=O)c23)[C@@H]2CCC[C@@H]2C(=O)N(C)C4)C1]

(IV)

(3aR,14aR)-5,10-dimethyl-3,3a,5,6,9,10,11,12-octahydro-1H-cyclopenta[f]pyrido[4",3":4',5']thieno[2',3':4,5]pyrimido[1,2-a][1,4]diazepine-4,13(2H,14aH)-dione:

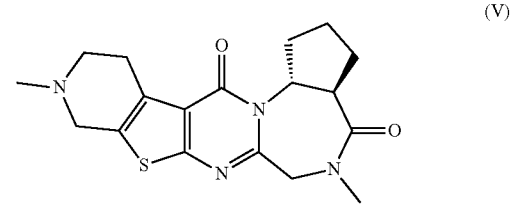 [SMILES: CN1CCc2c(sc3nc4n(c(=O)c23)[C@@H]2CCC[C@H]2C(=O)N(C)C4)C1]

(V)

and
(3aS,14aS)-5,10-dimethyl-3,3a,5,6,9,10,11,12-octahydro-1H-cyclopenta[ft]pyrido[4",3":4',5']thieno[2',3':4,5]pyrimido[1,2-a][1,4]diazepine-4,13(2H,14aH)-dione:

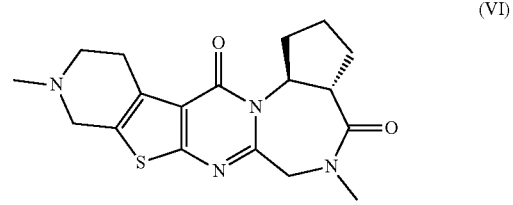 [SMILES: CN1CCc2c(sc3nc4n(c(=O)c23)[C@H]2CCC[C@@H]2C(=O)N(C)C4)C1]

(VI)

or a pharmaceutically acceptable salt thereof.
2. 3-Fluoro-6,11-dimethyl-6,7,10,11,12,13-hexahydrobenzo[f]pyrido[4",3":4',5']thieno[2',3':4,5]pyrimido[1,2-a][1,4]diazepine-5,14-dione or a pharmaceutically acceptable salt thereof according to claim 1:

(I)

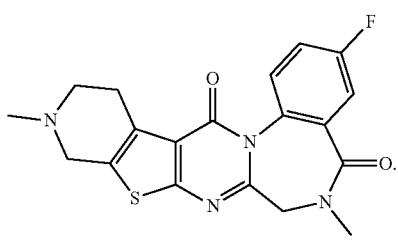

3. 5,10-Dimethyl-5,6,9,10,11,12-hexahydropyrido[4",3":4',5']thieno[2',3':4,5]pyrimido[1,2-a]thieno[2,3-f][1,4]diazepine-4,13-dione or a pharmaceutically acceptable salt thereof according to claim 1:

(II)

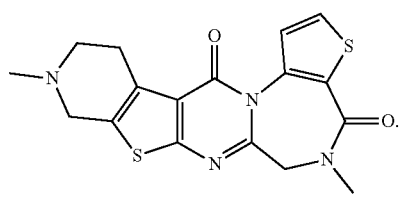

4. 5,10-Dimethyl-5,6,9,10,11,12-hexahydropyrido[4",3":4',5']thieno[2',3':4,5]pyrimido[1,2-a]thieno[3,2-f][1,4]diazepine-4,13-dione or a pharmaceutically acceptable salt thereof according to claim 1:

(III)

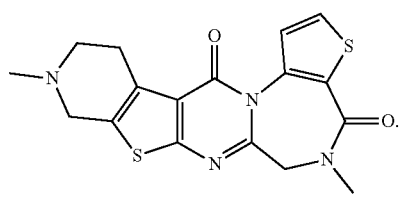

5. (3aS,14aR)-5,10-Dimethyl-3,3a,5,6,9,10,11,12-octahydro-1H-cyclopenta[f]pyrido[4",3":4',5']thieno[2',3':4,5]pyrimido[1,2-a][1,4]diazepine-4,13(2H,14aH)-dione or a pharmaceutically acceptable salt thereof according to claim 1:

(IV)

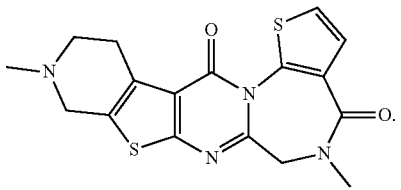

6. (3aR,14aR)-5,10-Dimethyl-3,3a,5,6,9,10,11,12-octahydro-1H-cyclopenta[f]pyrido[4",3":4',5']thieno[2',3':4,5]pyrimido[1,2-a][1,4]diazepine-4,13(2H,14aH)-dione or a pharmaceutically acceptable salt thereof according to claim 1:

(V)

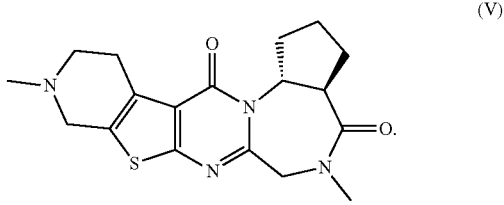 [SMILES: CN1CCc2c(sc3nc4n(c(=O)c23)[C@@H]2CCC[C@H]2C(=O)N(C)C4)C1]

7. (3aS,14aS)-5,10-DDimethyl-3,3a,5,6,9,10,11,12-octahydro-1H-cyclopenta[f]pyrido[4'",3":4',5']thieno[2',3':4,5]pyrimido[1,2-a][1,4]diazepine-4,13(2H,14aH)-dione or a pharmaceutically acceptable salt thereof according to claim 1:

(VI)

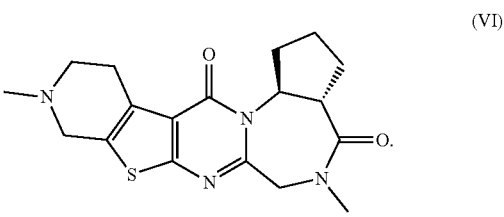 [SMILES: CN1CCc2c(sc3nc4n(c(=O)c23)[C@H]2CCC[C@@H]2C(=O)N(C)C4)C1]

8. A pharmaceutical composition comprising the compound or pharmaceutically acceptable salt thereof according to claim 1 and one or more pharmaceutically acceptable additives.

9. A method of treating a disease selected from a group consisting of Alzheimer's disease, Dementia with Lewy bodies and Parkinson disease with dementia comprising administering the compound or pharmaceutically acceptable salt thereof according to claim 1 to a patient in need thereof.

10. The method according to claim 9 wherein the disease is Alzheimer's disease.

11. The method according to claim 9 wherein the disease is Dementia with Lewy bodies.

12. The method according to claim 9 wherein the disease is Parkinson disease with dementia.

* * * * *

UNITED STATES PATENT AND TRADEMARK OFFICE
CERTIFICATE OF CORRECTION

PATENT NO. : 10,239,889 B1
APPLICATION NO. : 16/122116
DATED : March 26, 2019
INVENTOR(S) : Yoshiaki Ohashi et al.

It is certified that error appears in the above-identified patent and that said Letters Patent is hereby corrected as shown below:

On the Title Page

In the Abstract, Column 2
Line 2, delete "(1)" and insert -- (I) --.

OTHER PUBLICATIONS, Page 2
Column 2
Line 41, after "tauopathy" insert -- mouse --.

In the Specification

Column 2
Line 21, delete "fimbria-fomrnix" and insert -- fimbria-fornix --.
Line 47, delete "Alzheiner's" and insert -- Alzheimer's --.

Column 4
Line 35, under "Citation List, Non-Patent Literature", delete "inP301S" and insert -- in P301S --.
Line 64, delete "et." and insert -- et --.

Column 5
Line 13, delete "and or" and insert -- and/or --.

Column 6
Line 14, delete "(2H, 14aH)-" and insert -- (2H,14aH)- --.

Column 11
Line 1, delete "(1)" and insert -- (I) --.
Line 6, delete "kg" and insert -- µg --.

Signed and Sealed this
Seventeenth Day of December, 2019

Andrei Iancu
*Director of the United States Patent and Trademark Office*

Column 12
Line 42, delete "Parallex" and insert -- Parallax --.
Line 44, delete "11," and insert -- IB, --.
Line 49, delete "Initiator+ TM" and insert -- Initiator+TM --.
Line 50, delete "Gel60" and insert -- Gel 60 --.
Line 54, delete "(Silicagel)" and insert -- (Silica gel) --.
Line 55, delete "2 L" and insert -- 2L --.
Line 56, delete "3 L" and insert -- 3L --.
Line 63, delete "2 L" and insert -- 2L --.
Line 63, delete "3 L" and insert -- 3L --.
Line 66, delete "2 L" and insert -- 2L --.
Line 67, delete "3 L" and insert -- 3L --.

Column 14
Line 6, delete "J" and insert -- J= --.

Column 15
Line 14, delete "11H)," insert -- 1H), --.
Line 52, delete "(1 S,2R)-" insert -- (1S,2R)- --.

Column 16
Lines 1-2, delete "-methloctahydrocyclopenta" and insert -- -methyloctahydrocyclopenta --.

Column 17
Line 22, delete "311)," and insert -- 3H), --.
Line 54, delete "-((1 S,2S" and insert -- -((1S,2S --.

Column 18
Lines 1-2, delete "-methyloctahdrocclopentae]" and insert -- -methyloctahydrocyclopenta[e] --.
Lines 6-7, delete "-((1 S,2S)-" and insert -- -((1S,2S)- --.
Line 32, delete "]pyrimido 1," and insert -- ]pyrimido[1, --.

Column 19
Line 17, delete "311)," and insert -- 3H), --.
Line 20, delete "J" and insert -- J= --.

Column 21
Line 63, delete "21H)," and insert -- 2H), --.
Line 66, delete "1H-1)." and insert -- 1H). --.

Column 23
Line 9, delete "(p×15" and insert -- φ×15 --.
Line 20, delete "-H-" and insert -- -1H- --.

Column 26
Line 38, delete "Fischer344" and insert -- Fischer 344 --.

CERTIFICATE OF CORRECTION (continued)
U.S. Pat. No. 10,239,889 B1

Line 47, delete "cistema" and insert -- cisterna --.

Column 28
Line 13, delete "Usi Ng Fimbria-Fomix" and insert -- Using Fimbria-Fornix --.
Line 14, delete "Fimbria-Fomix" and insert -- Fimbria-Fornix --.
Line 25, delete "fimbria-fornmix." and insert -- fimbria-fornix. --.

Column 29
Line 32, delete "77.1" and insert -- 77.2 --.

In the Claims

Column 30
Claim 1, Line 2, delete "[3,2-]" and insert -- [3,2-f] --.
Claim 1, Line 48, delete "[ft]" and insert -- [f] --.

Column 32
Claim 7, Line 20, delete "DDimethyl" and insert -- Dimethyl --.
Claim 7, Line 21, delete "[4''',3":4',5']" and insert -- [4",3"4',5'] --.